(12) United States Patent
Beight et al.

(10) Patent No.: US 6,872,743 B2
(45) Date of Patent: *Mar. 29, 2005

(54) SPLA$_2$ INHIBITORS

(75) Inventors: Douglas Wade Beight, Frankfort, IN (US); Michael Dean Kinnick, Indianapolis, IN (US); Ho-Shen Lin, Indianapolis, IN (US); John Michael Morin, Jr., Brownsburg, IN (US); Michael Enrico Richett, Indianapolis, IN (US); Daniel Jon Sall, Greenwood, IN (US); Jason Scott Sawyer, Indianapolis, IN (US)

(73) Assignee: Eli Lilly and Company, Indianapolis, IN (US)

( * ) Notice: Subject to any disclaimer, the term of this patent is extended or adjusted under 35 U.S.C. 154(b) by 0 days.

This patent is subject to a terminal disclaimer.

(21) Appl. No.: 10/450,633

(22) PCT Filed: Dec. 6, 2001

(86) PCT No.: PCT/US01/43185

§ 371 (c)(1),
(2), (4) Date: Jun. 16, 2003

(87) PCT Pub. No.: WO02/50034

PCT Pub. Date: Jun. 27, 2002

(65) Prior Publication Data

US 2004/0063941 A1 Apr. 1, 2004

Related U.S. Application Data

(60) Provisional application No. 60/256,396, filed on Dec. 18, 2000.

(51) Int. Cl.$^7$ .................... A61K 31/403; C07D 209/56
(52) U.S. Cl. .................... 514/410; 548/420; 546/70; 544/233; 544/247; 514/248; 514/257; 514/285
(58) Field of Search ................... 514/410, 285, 514/257, 248; 548/420; 546/70; 544/233, 247

(56) References Cited

FOREIGN PATENT DOCUMENTS

| EP | 0 950 657 | 10/1999 |
|---|---|---|
| WO | WO 98/18464 | 5/1998 |

*Primary Examiner*—Charanjit S. Aulakh
(74) *Attorney, Agent, or Firm*—Francis O. Ginah

(57) ABSTRACT

A novel class of tetracyclic compounds represented by the formula I wherein R1, R2, R3, R4, R5, R6, R7, A, B, C, D, E, and n are as defined is disclosed together with the use of such compounds for inhibiting sPLA2 mediated release of fatty acids for treatment of Inflammatory Diseases such as septic shock.

18 Claims, No Drawings

SPLA₂ INHIBITORS

This application claims benefit of U.S. Provisional Application No. 60/256,396, filed Dec. 18, 2000 and PCT International Application No. PCT/US01/43185, filed Dec. 6, 2001.

This invention relates to novel tetracyclic compounds useful for Inflammatory Diseases.

The structure and physical properties of human non-pancreatic secretory phospholipase $A_2$ (hereinafter called, "sPLA₂") has been thoroughly described in two articles, namely, "Cloning and Recombinant Expression of Phospholipase $A_2$ Present in Rheumatoid Arthritic Synovial Fluid" by Seilhamer, Jeffrey J.; Pruzanski, Waldemar; Vadas Peter; Plant, Shelley; Miller, Judy A.; Kloss, Jean; and Johnson, Lorin K.; *The Journal of Biological Chemistry*, Vol. 264, No. 10, Issue of April 5, pp. 5335–5338, 1989; and "Structure and Properties of a Human Non-pancreatic Phospholipase $A_2$" by Kramer, Ruth M.; Hession, Catherine; Johansen, Berit; Hayes, Gretchen; McGray, Paula; Chow, E. Pingchang; Tizard, Richard; and Pepinsky, R. Blake; *The Journal of Biological Chemistry*, Vol. 264, No. 10, Issue of April 5, pp. 5768–5775, 1989; the disclosures of which are incorporated herein by reference.

It is believed that sPLA₂ is a rate limiting enzyme in the arachidonic acid cascade which hydrolyzes membrane phospholipids. Thus, it is important to develop compounds, which inhibit SPLA₂ mediated release of fatty acids (e.g., arachidonic acid). Such compounds would be of value in general treatment of conditions induced and/or maintained by overproduction of sPLA₂; such as sepsis or rheumatoid arthritis.

It is desirable to develop new compounds and treatments for sPLA₂ induced diseases.

This invention provides novel tetracyclic compounds of formula (I), or a pharmaceutically acceptable salt, solvate, or prodrug derivative thereof;

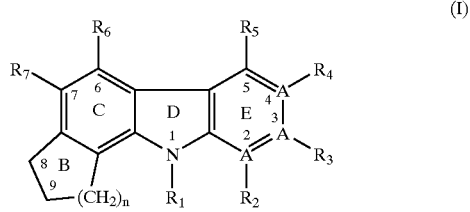

(I)

wherein;

A is independently C, or N;

n is 1, 2 or 3;

B, C, D, and E are ring identifiers; and the ring E has 1 to 3 double bonds (including double bond due to indole formed by combination of rings C and D); and the B ring has 0 to 2 double bonds; and wherein $R_1$, $R_2$, $R_3$, $R_4$, $R_5$, $R_6$, $R_7$ are as described infra having potency and selective effectiveness as inhibitors of mammalian sPLA₂.

This invention relates to the use of novel tetracyclic compounds of formula I useful in the treatment and/or prevention of Inflammatory Diseases.

This invention is also the use of novel tetracyclic compounds of formula I to inhibit mammalian SPLA₂ mediated release of fatty acids.

This invention is also a pharmaceutical composition containing any of the tetracyclic compounds of the invention.

The present invention relates to a pharmaceutical formulation comprising the novel tetracyclic compounds of the invention.

I. Definitions

The term, "Inflammatory Diseases" refers to diseases such as inflammatory bowel disease, sepsis, septic shock, adult respiratory distress syndrome, pancreatitis, trauma-induced shock, asthma, bronchial asthma, allergic rhinitis, rheumatoid arthritis, cystic fibrosis, stroke, acute bronchitis, chronic bronchitis, acute bronchiolitis, chronic bronchiolitis, osteoarthritis, gout, spondylarthropathris, ankylosing spondylitis, Reiter's syndrome, psoriatic arthropathy, enteropathic spondylitis, Juvenile arthropathy or juvenile ankylosing spondylitis, Reactive arthropathy, infectious or post-infectious arthritis, gonoccocal arthritis, tuberculous arthritis, viral arthritis, fungal arthritis, syphilitic arthritis, Lyme disease, arthritis associated with "vasculitic syndromes", polyarteritis nodosa, hypersensitivity vasculitis, Luegenec's granulomatosis, polymyalgin rheumatica, joint cell arthritis, calcium crystal deposition arthropathris, pseudo gout, non-articular rheumatism, bursitis, tenosynomitis, epicondylitis (tennis elbow), carpal tunnel syndrome, repetitive use injury (typing), miscellaneous forms of arthritis, neuropathic joint disease (charco and joint), hemarthrosis (hemarthrosic), Henoch-Schonlein Purpura, hypertrophic osteoarthropathy, multicentric reticulohistiocytosis, arthritis associated with certain diseases, surcoilosis, hemochromatosis, sickle cell disease and other hemoglobinopathries, hyperlipoproteineimia, hypogammaglobulinemia, hyperparathyroidism, acromegaly, familial Mediterranean fever, Behat's Disease, systemic lupus erythrematosis, or relapsing polychondritis and related diseases which comprises administering to a mammal in need of such treatment a therapeutically effective amount of the compound of formula I in an amount sufficient to inhibit sPLA₂ mediated release of fatty acid and to thereby inhibit or prevent the arachidonic acid cascade and its deleterious products.

The terms, "mammal" and "mammalian" include human and domesticated quadrupeds.

The term, "tetracyclic", or "tetracyclic nucleus" as used herein refers to a nucleus (having numbered positions) with the structural formula (X):

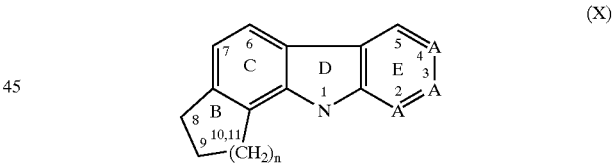

(X)

wherein, A is a carbon or nitrogen atom with the appropriate number of hydrogen atoms or non-interfering substituents appended; and the letters B, C, D and E are ring identifiers.

The Tetracyclic Compounds of the Invention Employ Certain Defining Terms as Follows:

The term, "alkyl" by itself or as part of another substituent means, unless otherwise defined, a straight or branched chain monovalent hydrocarbon radical such as methyl, ethyl, n-propyl, isopropyl, n-butyl, tertiary butyl, sec-butyl, n-pentyl, and n-hexyl.

The term, "alkenyl" employed alone or in combination with other terms means a straight chain or branched monovalent hydrocarbon group having the stated number ranges of carbon atoms, and typified by groups such as vinyl, propenyl, crotonyl, isopentenyl, and various butenyl isomers.

The term, "hydrocarbyl" means an organic group containing only carbon and hydrogen.

The term, "halo" means fluoro, chloro, bromo, or iodo.

The term, heterocyclic radical, refers to radicals derived from monocyclic or polycyclic, saturated or unsaturated, substituted or unsubstituted heterocyclic nuclei having 5 to 14 ring atoms and containing from 1 to 3 hetero atoms selected from the group consisting of nitrogen, oxygen or sulfur. Typical heterocyclic radicals are pyrrolyl, pyrrolodinyl, piperidinyl, furanyl, thiophenyl, pyrazolyl, imidazolyl, phenylimidazolyl, triazolyl, isoxazolyl, oxazolyl, thiazolyl, thiadiazolyl, benzo(b)thiophenyl, carbazolyl, norharmanyl, azabenzo(b)thiophenyl, benzofuranyl, dibenzofuranyl, dibenzothiophenyl, indazolyl, imidazo(1.2-A)pyridinyl, benzotriazolyl, anthranilyl, 1,2-benzisoxazolyl, benzoxazolyl, benzothiazolyl, purinyl, pyridinyl, dipyridylyl, phenylpyridinyl, benzylpyridinyl, pyrimidinyl, phenylpyrimidinyl, pyrazinyl, 1,3,5-triazinyl, quinolinyl, phthalazinyl, quinazolinyl, morpholino, thiomorpholino, homopiperazinyl, tetrahydrofuranyl, tetrahydropyranyl, oxacanyl, 1,3-dioxolanyl, 1,3-dioxanyl, 1,4-dioxanyl, tetrahydrothiophenyl, pentamethylenesulfadyl, 1,3-dithianyl, 1,4-dithianyl, 1,4-thioxanyl, azetidinyl, hexamethyleneiminium, heptamethyleneiminium, piperazinyl and quinoxalinyl.

The term, "carbocyclic radical" refers to radicals derived from a saturated or unsaturated, substituted or unsubstituted 5 to 14 membered organic nucleus whose ring forming atoms (other than hydrogen) are solely carbon atoms. Typical carbocyclic radicals are cycloalkyl, cycloalkenyl, phenyl, spiro[5.5]undecanyl, naphthyl, norbornanyl, bicycloheptadienyl, toluyl, benzyl, xylenyl, indenyl, stilbenyl, terphenylyl, diphenylethylenyl, phenylcyclohexenyl, acenaphthylenyl, anthracenyl, biphenyl, dibenzylyl and related dibenzylyl homologues represented by the formula (a):

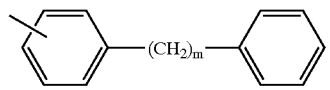

(a)

where m is a number from 0 to 8.

The terms, "non-interfering substituent", or "non-interfering groups" refer to radicals suitable for substitution at positions 1, 2, 3, 4, 7, 8, 9 and/or 10 of the tetracyclic nucleus and on other nucleus substituents (as hereinafter described for Formula I), and radicals suitable for substitution on the heterocyclic radical and carbocyclic radical as defined above. Illustrative non-interfering radicals are $C_1-C_8$ alkyl, $C_2-C_8$ alkenyl, $C_2-C_8$ alkynyl, $C_7-C_{12}$ aralkyl, $C_7-C_{12}$ alkaryl, $C_3-C_8$ cycloalkyl, $C_3-C_8$ cycloalkenyl, phenyl, toluyl, xylenyl, biphenyl, $C_1-C_8$ alkoxy, $C_2-C_8$ alkenyloxy, $C_2-C_8$ alkynyloxy, $C_2-C_{12}$ alkoxyalkyl, $C_2-C_{12}$ alkoxyalkyloxy, $C_2-C_{12}$ alkylcarbonyl, $C_2-C_{12}$ alkylcarbonylamino, $C_2-C_{12}$ alkoxyamino, $C_2-C_{12}$ alkoxyaminocarbonyl, $C_1-C_{12}$ alkylamino, $C_1-C_6$ alkylthio, $C_2-C_{12}$ alkylthiocarbonyl, $C_1-C_8$ alkylsulfinyl, $C_1-C_8$ alkylsulfonyl, $C_2-C_8$ haloalkoxy, $C_1-C_8$ haloalkylsulfonyl, $C_2-C_8$ haloalkyl, $C_1-C_8$ hydroxyalkyl, —C(O)O($C_1-C_8$ alkyl), —($CH_2$)$_n$—O—($C_1-C_8$ alkyl), benzyloxy, phenoxy, phenylthio, —(CONHSO$_2$R), —CHO, amino, amidino, bromo, carbamyl, carboxyl, carbalkoxy, —($CH_2$)$_n$—CO$_2$H, chloro, cyano, cyanoguanidinyl, fluoro, guanidino, hydrazide, hydrazino, hydrazido, hydroxy, hydroxyamino, iodo, nitro, phosphono, —SO$_3$H, thioacetal, thiocarbonyl, and carbonyl; where n is from 1 to 8 and R is $C_1-C_8$ alkyl.

The term, "organic substituent" refers to a monovalent radical consisting of carbon and hydrogen with or without oxygen, nitrogen, sulfur, halogen, or other elements. Illustrative organic substituents are $C_1-C_8$ alkyl, aryl, $C_7-C_{14}$ aralkyl, $C_7-C_{14}$ alkaryl, $C_3-C_8$ cycloalkyl, $C_1-C_8$ alkoxyalkyl and these groups substituted with halogen, —CF$_3$, —OH, $C_1-C_8$ alkyl, amino, carbonyl, and —CN.

The term "substituted group" is an organic group substituted with one or more non-interfering substituents.

As used herein the terms "group", "radical" and "fragment" are synonymous and are intended to indicate functional groups or fragments of molecules attachable to a bond or other fragments of molecules. For example, acetamide group represents the acetamide fragment or radical. Structures of groups, radicals or fragments unattached to the tetracyclic nucleus have been drawn to show the first line as a connecting bond only. Thus, the group

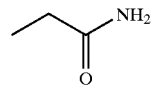

indicates the acetamide radical not the propanamide radical unless otherwise indicated.

The term, "N-hydroxyfunctional amide group" is represented by the formula:

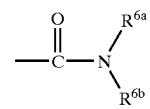

wherein $R^{6a}$ is selected from the group consisting of OH, ($C_1-C_6$)alkoxy, and aryloxy; and wherein $R^{6b}$ is hydrogen or an organic substituent selected from the group consisting of $C_1-C_8$ alkyl, aryl, $C_7-C_{14}$ aralkyl, $C_7-C_{14}$ alkaryl, $C_3-C_8$ cycloalkyl, $C_1-C_8$ alkoxyalkyl and these groups substituted with halogen, —CF$_3$, —OH, $C_1-C_8$ alkyl, amino, carbonyl, and —CN.

The phrase, "N-hydroxyfunctional amide linker" refers to a divalent linking group symbolized as, -($L_h$)-, which has the function of joining the 6- or 7-position of the tetracyclic nucleus to an N-hydroxyfunctional amide group in the general relationship:

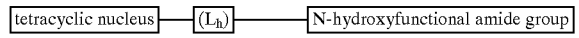

The words, "hydroxyfunctional amide linker length", refer to the number of atoms (excluding hydrogen) in the shortest chain of the linking group -($L_h$)- that connects the 6- or 7-position of the tetracyclic nucleus with the N-hydroxyfunctional amide group. The presence of a carbocyclic ring in -($L_h$)- counts as the number of atoms approximately equivalent to the calculated diameter of the carbocyclic ring. Thus, a benzene or cyclohexane ring in the acid linker counts as 2 atoms in calculating the length of -($L_h$)-. Illustrative "N-hydroxyfunctional amide linker" groups are;

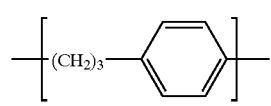

(a)

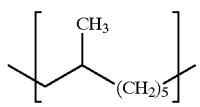
(b)

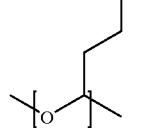
(c)

wherein, groups (a), (b) and (c) have acid linker lengths of 5, 7, and 2, respectively.

The term, "(acidic group)" means an organic group which when attached to a tetracyclic nucleus at the 6- or 7-position, through suitable linking atoms (hereinafter defined as the "acid linker"), acts as a proton donor capable of hydrogen bonding. Illustrative of an (acidic group) are the following:

-5-tetrazolyl,

—SO$_3$H,

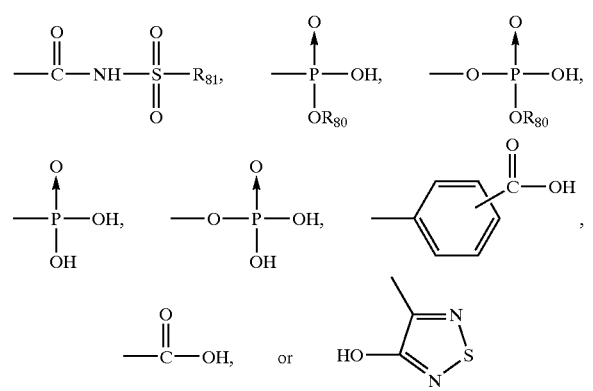

where n is 1 to 8, $R_{80}$ is a metal or $C_1$–$C_8$ and $R_{81}$ is an organic substituent or —CF$_3$.

The words, "acid linker" refer to a divalent linking group symbolized as, -(L$_a$)-, which has the function of joining the 6- or 7-position of the tetracyclic nucleus to an acidic group in the general relationship:

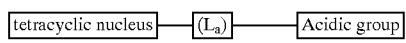

The words, "acid linker length", refer to the number of atoms (excluding hydrogen) in the shortest chain of the linking group -(L$_a$)- that connects the 6- or 7-position of the tetracyclic nucleus with the acidic group. The presence of a carbocyclic ring in -L$_{(a)}$- counts as the number of atoms approximately equivalent to the calculated diameter of the carbocyclic ring. Thus, a benzene or cyclohexane ring in the acid linker counts as 2 atoms in calculating the length of -L$_{(a)}$-. Illustrative acid linker groups include;

(a)

(b)

(c)

wherein, groups (a), (b), and (c) have acid linker lengths of 5, 7, and 2, respectively.

The term, "acylamino acid group" is represented by the formula:

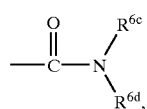

wherein $R^{6c}$ is selected from the group consisting of H, (C$_1$–C$_6$)alkyl, (C$_1$–C$_6$)alkoxy, heteroaryl and aryl, —CF$_3$; and wherein NR$^{6d}$ is an amino acid residue of either a natural or unnatural amino acid with the nitrogen atom being part of the amino group of the amino acid. A typical amino acid is selected from the group comprising isoleucine, valine, phenylalanine, aspartic acid, leucine, glycine, asparagine, cysteine, glutamine, glutamic acid, histidine, lysine, methionine, serine, threonine, tryptophan, tyrosine and derivatives thereof. Contemplated within the definition of amino acid are l-proline, d-proline and derivatives thereof. Also contemplated within the definition of amino acids are peptides, polypeptides and derivatives thereof.

The term, "amino acid residue" refers to the portion of the amino acid group coupled at the nitrogen atom of the amino terminus. It is the amino acid less a hydrogen atom from the amino terminus. It is further illustrated as used herein for the amino acid alanine attached at the nitrogen atom as shown below:

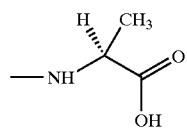

The words, "acylamino acid linker" refer to a divalent linking group symbolized as, -(L$_c$)-, which has the function of joining the 6- or 7-position of the tetracyclic nucleus to an acylamino acid group in the general relationship:

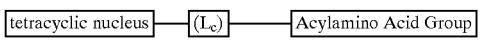

The words, "acylamino acid linker length", refer to the number of atoms (excluding hydrogen) in the shortest chain of the linking group -($L_c$)- that connects the 6- or 7-position of the tetracyclic nucleus with the acylamino acid group. The presence of a carbocyclic ring in -($L_c$)- counts as the number of atoms approximately equivalent to the calculated diameter of the carbocyclic ring. Thus, a benzene or cyclohexane ring in the acid linker counts as 2 atoms in calculating the length of -($L_c$)-. Illustrative "acylamino acid linker groups" include:

(a)

$$-\left[(CH_2)_3-\bigcirc-\right]-$$

(b)

$$-\left[\begin{matrix}CH_3\\|\\(CH_2)_5\end{matrix}\right]-$$

(c)

(structure showing phenyl-CH2-CH2-C(CH3)(O-)-)

wherein, groups (a), (b) and (c) have acid linker lengths of 5, 7, and 2, respectively.

The Term, "amine", includes primary, secondary and tertiary amines.

The term, "alkylene chain of 1 or 2 carbon atoms" refers to the divalent radicals, —$CH_2$—$CH_2$— and —$CH_2$—.

The term, "group containing 1 to 10 non-hydrogen atoms" refers to relatively small groups which form substituents at the 2-position of the tetracyclic nucleus, said groups may contain non-hydrogen atoms alone, or non-hydrogen atoms plus hydrogen atoms as required to satisfy the unsubstituted valence of the non-hydrogen atoms, for example; (i) groups absent hydrogen which contain no more than 4 non-hydrogen atoms such as —$CF_3$, —Cl, —Br, —$NO_2$, —CN, —$SO_3$; and (ii) groups having hydrogen atoms which contain less than 4 non-hydrogen atoms such as —$CH_3$, —$C_2H_5$, and —CH=$CH_2$.

The term "oxime amide" means the radical, —C(=NOR)—C(O)$NH_2$.

The term "thio-oxime amide" means the radical —C(=NOR)—C(S)—$NH_2$.

The term "spiro[5.5]undecanyl" refers to the group represented by the formula;

(spiro bicyclic structure)

II. The Tetracyclic Compounds of the Invention

The present invention provides a novel class of tetracyclic compounds useful as sPLA$_2$ inhibitors for the treatment of inflammation and inflammatory diseases. Subclasses of tetracyclic compounds of this invention include tetracyclic oxyacid derivatives, tetracyclic-5-oxime amide oxyacid derivatives, tetracyclic-5-acetamide oxyacid derivatives, tetracyclic-5-glyoxylamide N-hydroxyfunctional amide derivatives, tetracyclic-5-oxime amide N-hydroxyfunctional amide derivatives, tetracyclic-5-acetamide hydroxyfunctional amide derivatives, tetracyclic-5-glyoxylamide acylamino acid derivatives, tetracyclic-5-oxime amide acylamino acid derivatives, tetracyclic-5-acetamide acylamino acid derivatives.

The compounds of the invention have the general formula (I) or a pharmaceutically acceptable salt, solvate or prodrug thereof;

(I)

(tetracyclic structure with rings B, C, D, E and substituents $R_1$–$R_7$, A positions, and (CH$_2$)$_n$)

wherein;

n is 1, 2 or 3

B, C, D, and E are ring identifiers and wherein the B ring is either saturated or unsaturated with up to three double bonds with the appropriate number of hydrogen or non-interfering groups appended;

The E ring is either saturated or unsaturated with 1 to 3 double bonds including the indole ring double bond, and the appropriate number of hydrogen atoms or non-interfering groups appended;

A is independently C, or N with the appropriate number of hydrogen atoms or non-interfering groups appended.

$R_1$ is selected from groups (a), (b), or (c) wherein;
  (a) is $C_7$–$C_{20}$ alkyl, $C_7$–$C_{20}$ haloalkyl, $C_7$–$C_{20}$ alkenyl, $C_7$–$C_{20}$ alkynyl, aryl, $C_7$–$C_{20}$ alkylaryl, carbocyclic radical, or heterocyclic radical, or
  (b) is a member of (a) substituted with one or more independently selected non-interfering substituents;
  (c) is the group -(L)-$R_{80}$; where, -(L)- is a divalent linking group of 1 to 12 atoms selected from carbon, hydrogen, oxygen, nitrogen, and sulfur; wherein the combination of atoms in -(L)- are selected from the group consisting of (i) carbon and hydrogen only, (ii) sulfur only, (iii) oxygen only, (iv) nitrogen and hydrogen only, (v) carbon, hydrogen, and sulfur only, and (vi) and carbon, hydrogen, and oxygen only; and where $R_{80}$ is a group selected from (a) or (b);

$R_2$, $R_3$ and $R_4$ are each independently hydrogen, or a group containing 1 to 10 non-hydrogen atoms plus any required hydrogen atoms provided A is carbon; and when A is nitrogen $R_2$, $R_3$, and $R_4$ are the appropriate number of hydrogen atoms or non-interfering groups from 0 to 2 (i.e. $R_2$, $R_3$, and $R_4$ are non-existent where A is a nitrogen atom);

$R_5$ is -($L_5$)-Z, where -($L_5$)- is a divalent linker group selected from a bond, or a divalent group selected from:

$$-\underset{H_2}{C}-, \quad -O-, \quad -S-, \quad -\underset{H}{N}-, \quad \text{or} \quad -\underset{\parallel}{\overset{\parallel}{C}}-\\ \phantom{xxxxxxxxxxxxxxxxxxxxxxxxxxxxxxxx}O$$

and Z is selected from an amide, thioamide, oxime amide, oxime thioamide, glyoxylamide, hydrazide, or acetamide group represented by the formulae,

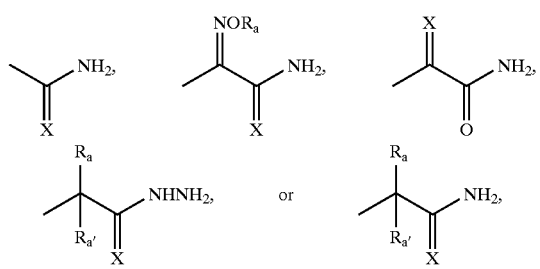

wherein X is oxygen or sulfur, $R_a$ and $R_{a'}$ are independently selected from hydrogen, $C_1$–$C_8$ alkyl, aryl, $C_1$–$C_8$ alkaryl, $C_1$–$C_8$ alkoxy, aralkyl and —CN;

$R_6$ is the group, hydrogen or $-L_{(a)}$-(acidic group) wherein $-L_{(a)}$-, is an acid linker having an acid linker length of 1 to 8;

or the group $-(L_h)$-(N-hydroxyfunctional amide group); wherein $-(L_h)$-, is an N-hydroxyfunctional amide linker having a N-hydroxyfunctional amide linker length of 1 to 8; and wherein a N-hydroxyfunctional amide group is represented by the formula:

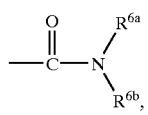

wherein Y is oxygen;

$R^{6a}$ is selected from the group consisting of OH, ($C_1$–$C_6$) alkoxy, and aryloxy; and wherein $R^{6b}$ is hydrogen or an organic substituent selected from the group consisting of $C_1$–$C_8$ alkyl, aryl, $C_7$–$C_{14}$ aralkyl, $C_7$–$C_{14}$ alkaryl, $C_3$–$C_8$ cycloalkyl, $C_1$–$C_8$ alkoxyalkyl and these groups substituted with halogen, —$CF_3$, —OH, $C_1$–$C_8$ alkyl, amino, carbonyl, and —CN;

or $R_6$ is the group $-(Lc)$-(acylamino acid group) wherein the "acylamino acid group" is represented by the formula:

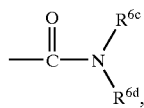

wherein $R^{6c}$ is selected from the group consisting of H, ($C_1$–$C_6$)alkyl, ($C_1$–$C_6$)alkoxy, heteroaryl and aryl, —$CF_3$; and wherein $NR^{6d}$ is an amino acid residue of either a natural or unnatural amino acid with the nitrogen atom being part of the amino group of the amino acid.

$R_7$ is selected from hydrogen, a non-interfering substituent, the group $-(L_h)$-(N-hydroxyfunctional amide group), or the group $-(L_c)$-acylamino acid group), or the group, $-L_{(a)}$-(acidic group); wherein $-L_{(a)}$-, is an acid linker having an acid linker length of 1 to 8; and provided that at least one of $R_6$ or $R_7$ is the group $-(L_h)$-(N-hydroxyfunctional amide group), or the group $-(L_c)$-acylamino acid group), or the group, $-L_{(a)}$-(acidic group).

$R_8$ and $R_9$ are each independently non-interfering groups.

Preferred Subgroups of Compounds of Formula (I)

A preferred subclass of compounds of formula I are those wherein A is carbon.

Another preferred subclass includes compounds of formula I wherein the B ring is 5- or 6-membered ring and the E ring is a benzene ring (i.e., all A are carbon). Also preferred is a subclass wherein the B and C rings combine to form a naphthalene ring system.

Preferred $R_1$ Substituents:

A preferred subclass of compounds of formula (I) are those where for $R_1$ the divalent linking group $-(L_1)$- is a group represented by any one of the following formulae (Ia), (Ib), (Ic), (Id), (Ie), or (If):

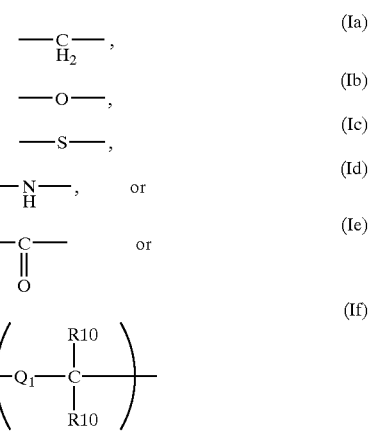

where $Q_1$ is a bond or any of the divalent groups (Ia), (Ib), (Ic), (Id), (Ie), and (If) and each $R_{10}$ is independently hydrogen, $C_{1-8}$ alkyl, $C_{1-8}$ haloalkyl or $C_{1-8}$ alkoxy.

Particularly preferred as the linking group $-(L_1)$- of $R_1$ is an alkylene chain of 1 or 2 carbon atoms, namely, —($CH_2$)— or —($CH_2$—$CH_2$)—.

The preferred group for $R_{11}$ is a substituted or unsubstituted group selected from the group consisting of $C_5$–$C_{14}$ cycloalkyl, $C_5$–$C_{14}$ cycloalkenyl, phenyl, naphthyl, norbornanyl, bicycloheptadienyl, toluyl, xylenyl, indenyl, stilbenyl, terphenylyl, diphenylethylenyl, phenylcyclohexenyl, acenaphthylenyl, and anthracenyl, biphenyl, bibenzylyl and related bibenzylyl homologues represented by the formula (a);

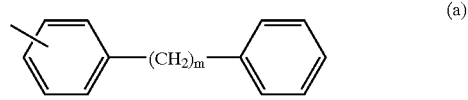

where m is a number from 1 to 8.

Particularly preferred are compounds wherein for $R_1$ the combined group $-(L_1)$-$R_{11}$ is selected from the group consisting of

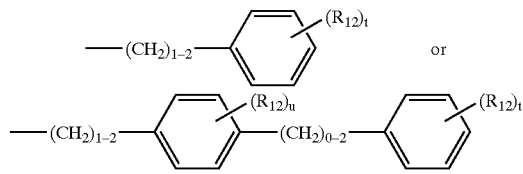

where $R_{12}$ is a radical independently selected from halo, $C_1$–$C_8$ alkyl, $C_1$–$C_8$ alkoxy, —S—($C_1$–$C_8$ alkyl), —O—($C_1$–$C_8$ alkyl) and $C_1$–$C_8$ haloalkyl where t is a number from 0 to 5 and u is a number from 0 to 4;

Also preferred for $R_1$ is the group $-(L_1)$-$R_{11}$; where, $-(L_1)$- is a divalent linking group of 1 to 8 atoms and where $R_{11}$ is a group selected from (a) or (b).

Preferred for $R_{11}$ is —$(CH_2)m$—$R^{12}$ wherein m is an integer from 1 to 6, and $R^{12}$ is (d) a group represented by the formula:

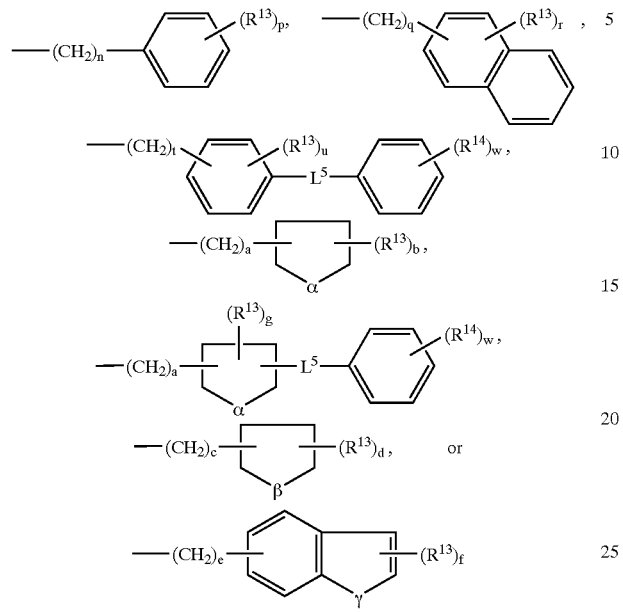

wherein a, c, e, n, q, and t are independently an integer from 0 to 2, $R^{13}$ and $R^{14}$ are independently selected from a halogen, $C_1$ to $C_8$ alkyl, $C_1$ to $C_8$ alkyloxy, $C_1$ to $C_8$ alkylthio, aryl, heteroaryl, and $C_1$ to $C_8$ haloalkyl, α is an oxygen atom or a sulfur atom, $L^5$ is a bond, —$(CH_2)v$—, —C=C—, —CC—, —O—, or —S—, v is an integer from 0 to 2, β is —$CH_2$— or —$(CH_2)_2$—, γ is an oxygen atom or a sulfur atom, b is an integer from 0 to 3, d is an integer from 0 to 4, f, p, and w are independently an integer from 0 to 5, r is an integer from 0 to 7, and u is an integer from 0 to 4, or is (e) a member of (d) substituted with at least one substituent selected from the group consisting of $C_1$ to $C_6$ alkyl, $C_1$ to $C_8$ alkyloxy, $C_1$ to $C_8$ haloalkyloxy, $C_1$ to $C_8$ haloalkyl, aryl, and a halogen.

Preferred $R_2$ Substituents:

When A is a carbon atom, $R_2$ is preferably selected from the group consisting of hydrogen, $C_1$–$C_4$ alkyl, $C_2$–$C_4$ alkenyl, —O—($C_1$–$C_3$ alkyl), —S—($C_1$–$C_3$ alkyl), —($C_3$–$C_4$)cycloalkyl —$CF_3$, halo, —$NO_2$, —CN, —$SO_3$. Particularly preferred $R_2$ groups are selected from hydrogen, methyl, ethyl, propyl, isopropyl, cyclopropyl, —F, —$CF_3$, —Cl, —Br, or —O—$CH_3$.

Preferred $R_3$/$R_4$ Substituents:

When A is a carbon atom, $R_3$ and $R_4$ are independently selected preferably from the group consisting of hydrogen, ($C_1$–$C_4$)alkyl, ($C_2$–$C_4$)alkenyl, —O—($C_1$–$C_3$ alkyl), —S—($C_1$–$C_3$ alkyl), —($C_3$–$C_4$)cycloalkyl —$CF_3$, halo, —$NO_2$, —CN, —$SO_3$. When A is a carbon atom, particularly preferred $R_3$ and $R_4$ groups are independently selected from hydrogen, methyl, ethyl, propyl, isopropyl, cyclopropyl, —F, —$CF_3$, —Cl, —Br, or —O—$CH_3$. When A is a nitrogen atom, $R_3$ and $R_4$ are preferably hydrogen or non-existent depending on the ring unsaturation.

Preferred $R_5$ Substituents:

A preferred subclass of compounds of formula (I) are those wherein X is oxygen.

Also preferred is a subclass of compounds of formula I wherein Z is a glyoxylamide (glyoxamide) group represented by

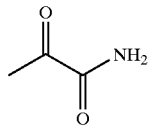

Another preferred subclass of compounds of formula (I) is the subclass wherein Z is an amide group

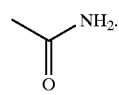

Another preferred subclass of compounds of formula (I) are those wherein Z is an oxime amide group.

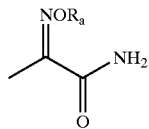

Also preferred are compounds of formula (I) wherein Z is an acetamide group represented by the formulae:

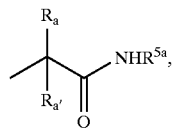

wherein $R_a$ and $R_{a'}$ are independently selected from hydrogen, ($C_1$–$C_8$)alkyl, aryl, ($C_1$–$C_8$)alkaryl, ($C_1$–$C_8$) alkoxy, aralkyl and —CN, and $R^{5a}$ is hydrogen, methyl or ethyl. For the group $R_5$ it is most preferred that the linking group -($L_5$)- be a bond.

Preferred $R_6$ Substituents:

A preferred subclass of compounds of formula I are those wherein $R_6$ is a substituent selected from hydrogen, or the group, -L($_a$)-(acidic group); wherein -L($_a$)- is an acid linker; provided the acid linker group, -L($_a$)- for $R_6$ is selected from the group consisting of;

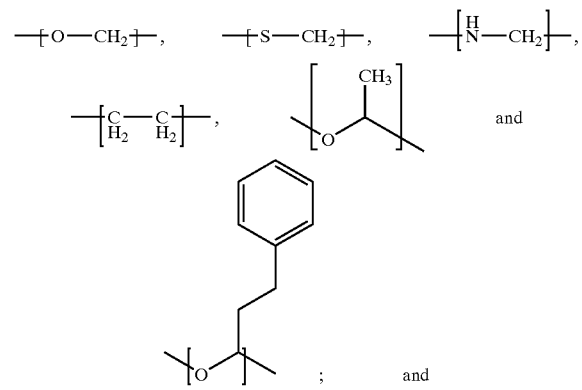

provided, that at least one of $R_6$ and $R_7$ must be the group, -L($_a$)-(acidic group) or the group -($L_h$)-(N-hydroxyfunctional amide group) or the group -(Lc)-(acylamino acid group), and wherein the (acidic group) on the group -L($_a$)-(acidic group) of $R_6$ or $R_7$ is selected from —$CO_2H$, $CO_2Na$, —$SO_3H$, or —P(O)(OH)$_2$;

Another preferred subclass subclass of compounds of formula I are those wherein $R_6$ is the group -(Lc)-(acylamino acid group)-, wherein -(Lc)- is an acylamino acid linker with an acylamino acid linker length of 2 or 3, and the "acylamino acid group" is represented by the formula:

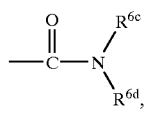

wherein $R^{6c}$ is selected from the group consisting of H, $(C_1-C_6)$alkyl, $(C_1-C_6)$alkoxy, heteroaryl and aryl, $-CF_3$; and wherein $NR^{6d}$ is an amino acid residue of either a natural or unnatural amino acid with the nitrogen atom being part of the amino group of the amino acid; and wherein the amino acid residue is derived from an amino acid selected from the group comprising isoleucine, valine, phenylalanine, aspartic acid, leucine, glycine, asparagine, cysteine, glutamine, glutamic acid, histidine, lysine, methionine, serine, threonine, tryptophan, tyrosine and derivatives thereof.

Another preferred subclass of compounds of formula (I) are those wherein $R_6$ is a substituent having an N-hydroxyfunctional amide linker with an N-hydroxyfunctional amide linker length of 2 or 3 and the N-hydroxyfunctional amide linker group, $-(L_h)-$, for $R_6$ is selected from a group represented by the formula;

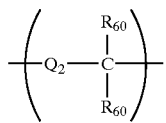

where $Q_2$ is selected from the group $-(CH_2)-$, $-O-$, $-NH-$, $-C(O)-$, and $-S-$, and each $R_{60}$ are independently selected from hydrogen, $C_1-C_8$ alkyl, aryl, $(C_1-C_8)$ alkaryl, $(C_1-C_8)$alkoxy, aralkyl, and halo.

Most preferred subclasses of compound of formula (I) are compounds where the acid linker -(La)-, or the N-hydroxyfunctional amide linker, $-(L_h)-$, or the acylamino acid linker $-(L_c)-$, for $R_6$ is independently selected from the specific groups;

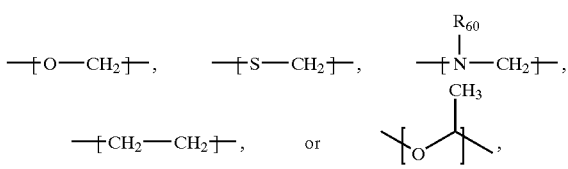

wherein $R_{60}$ is hydrogen or $C_1-C_8$ alkyl.

Preferred as the N-hydroxyfunctional amide group in the group $R_6$ is the group:

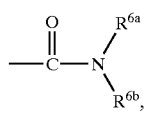

wherein $R^{6a}$ is selected from the group consisting of OH, $(C_1-C_6)$alkoxy and aryloxy; and
wherein $R^{6b}$ is an organic substituent selected from the group consisting of H, $C_1-C_8$ alkyl, aryl, $C_7-C_{14}$ aralkyl, $C_7-C_{14}$ alkaryl, $C_3-C_8$ cycloalkyl, $C_1-C_8$ alkoxyalkyl and these groups substituted with halogen, $-CF_3$, $-OH$, $C_1-C_8$ alkyl, amino, carbonyl, and $-CN$. A more preferred $R^{6a}$ group is selected from the group consisting of $-OH$, $-OCH_3$ and $-OC_2H_5$ while a more preferred $R^{6b}$ is selected from the group consisting of H, $C_1-C_8$ alkyl, aryl, $C_7-C_{14}$ aralkyl, $C_7-C_{14}$ alkaryl, $C_3-C_8$ cycloalkyl. A most preferred $R^{6b}$ is a group selected from H, $CH_3$, $C_2H_5$ and $C_3H_7$.

A salt or a prodrug derivative of the (N-hydroxyfunctional amide group) is also a suitable substituent.

Preferred $R_7$ Substituents:

A preferred $R_7$ substituent is the group hydrogen, a non-interfering substituent, or the group -(La)-(acidic group) wherein the preferred acid linker, -(La)-, for $R_7$ is selected from the group consisting of;

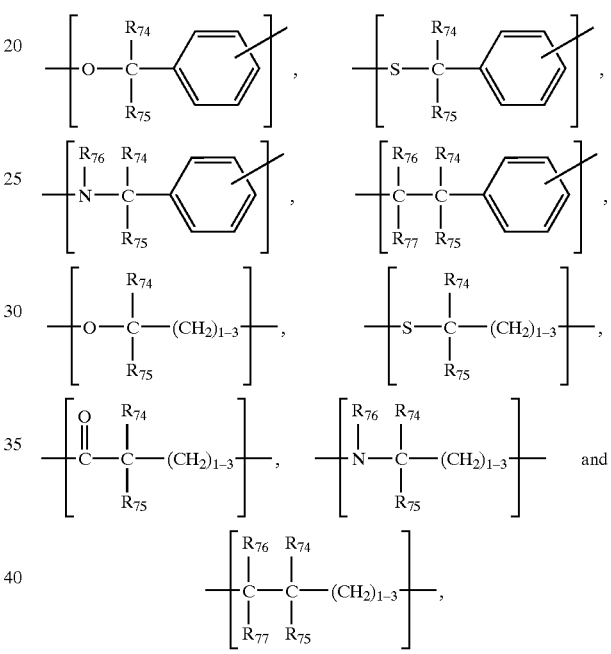

wherein $R_{74}$, $R_{75}$, $R_{76}$ and $R_{77}$ are each independently hydrogen, $C_1-C_8$ alkyl, $C_1-C_8$ haloalkyl, aryl, $C_1-C_8$ alkoxy, or halo. Preferred (acidic group) for $R_7$ is selected from the group consisting of $-CO_2H$, $-SO_3H$ and $-P(O)(OH)_2$. Most preferred for $R_7$ is the group hydrogen or a non-interfering substituent.

Most preferred compounds of the invention are those having the general formula (II) or (III) or (IV) or (V) or a pharmaceutically acceptable salt, solvate or prodrug derivative thereof;

II

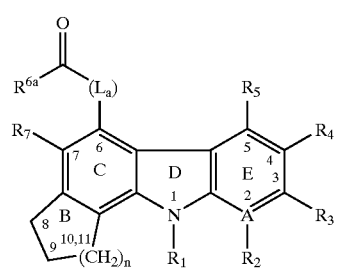

III

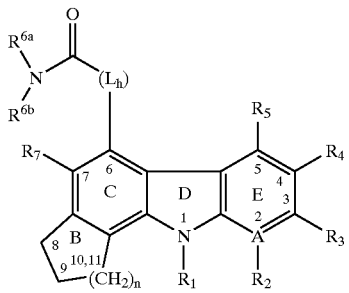

IV

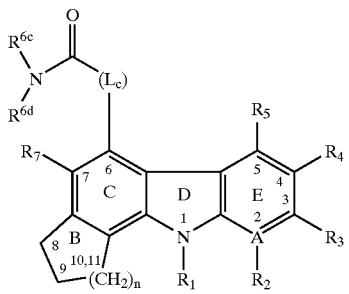

wherein;

A is carbon or nitrogen;

$R_1$ is selected from groups (a), (b), or (c) wherein;
  (a) is $C_7$–$C_{20}$ alkyl, $C_7$–$C_{20}$ haloalkyl, $C_7$–$C_{20}$ alkenyl, $C_7$–$C_{20}$ alkynyl, carbocyclic radical, or heterocyclic radical, or
  (b) is a member of (a) substituted with one or more independently selected non-interfering substituents;
  (c) is the group -(L)-$R_{80}$; where, -(L)- is a divalent linking group of 1 to 12 atoms selected from carbon, hydrogen, oxygen, nitrogen, and sulfur; wherein the combination of atoms in -(L)- are selected from the group consisting of (i) carbon and hydrogen only, (ii) sulfur only, (iii) oxygen only, (iv) nitrogen and hydrogen only, (v) carbon, hydrogen, and sulfur only, and (vi) and carbon, hydrogen, and oxygen only; and where $R_{80}$ is a group selected from (a) or (b);

$R_2$, $R_3$, and/or $R_4$ where applicable is selected from hydrogen, methyl, ethyl, propyl, isopropyl, cyclopropyl, —F, —$CF_3$, —Cl, —Br, or —O—$CH_3$;

$R_5$ is -($L_5$)-Z wherein ($L_5$) is preferably a bond and Z is selected from the group consisting of

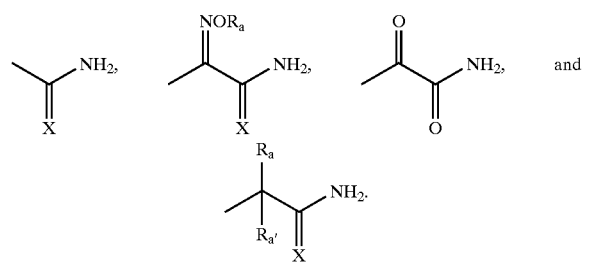

and

The Acidic Tetracyclic Compounds of the Invention

The acidic group tetracyclic compounds of the Invention are represented by a compound of formula (II) below:

II

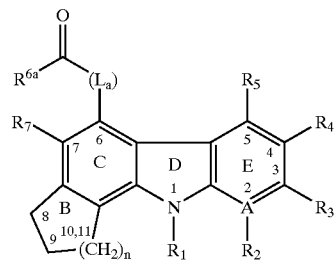

wherein A is carbon; and wherein ($L_a$) is an acid linker having an acid linker length of 2 or 3

$R_1$ is as described previously;

$R_2$ is as described previously;

$R_3$, and $R_4$ are as described previously;

$R_5$ is -($L_5$)-Z, where -($L_5$)- is a divalent linker group selected from a bond or a divalent group selected from:

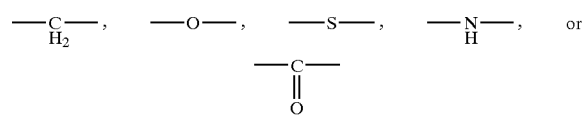

and Z is selected from an amide, thioamide or glyoxylamide, acetamide or thioacetamide, oxime, hydrazide radical (group) represented by the formulae,

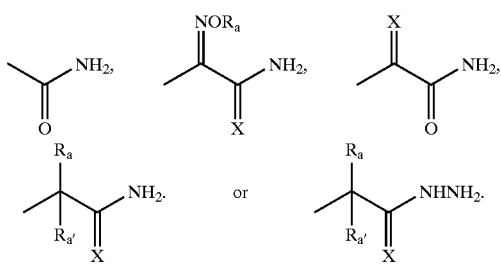

wherein X is oxygen or sulfur, $R_a$ and $R_{a'}$ are independently selected from hydrogen, $C_1$–$C_8$ alkyl, aryl, $C_1$–$C_8$ alkaryl;

$R_7$ is selected from hydrogen, a non-interfering substituent, or the group, -(La)-(acidic group); wherein -(La)-, is an acid linker having an acid linker length of 1 to 8.

The N-hydroxyfunctional Amide Tetracyclic Compounds of the Invention

The N-hydroxyfunctional amide tetracyclic Compounds of the Invention are represented by the general structure III below:

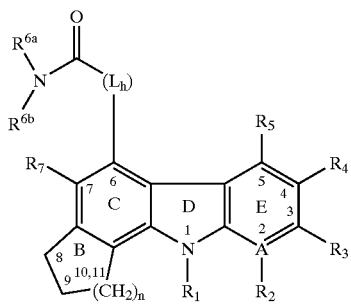

wherein A is carbon;

$R_1$, $R_2$, $R_3$ and $R_4$ are as described previously;

$R_5$ is -($L_5$)-Z, where -($L_5$)- is a divalent linker group selected from a bond or a divalent group selected from:

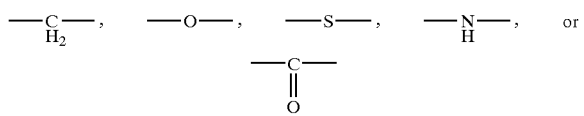

and Z is selected from an amide, thioamide or glyoxylamide, acetamide or thioacetamide, oxime, hydrazide radical (group) represented by the formulae,

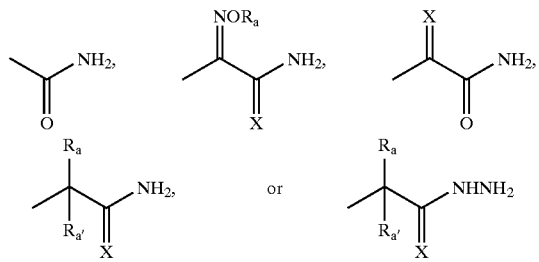

wherein, X is oxygen or sulfur, $R_a$ and $R_{a'}$ are independently selected from hydrogen, $C_1$–$C_8$ alkyl, aryl, $C_1$–$C_8$ alkaryl;

Preferred $R_6$ Substituents:

A preferred subclass of compounds of formula (III) are those wherein $R_6$ is a substituent having N-hydroxyfunctional amide linker with an N-hydroxyfunctional amide linker length of 2 or 3 and the N-hydroxyfunctional amide linker group, -($L_h$)-, for $R_6$ is selected from a group represented by the formula;

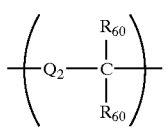

where $Q_2$ is selected from the group —(CH$_2$)—, —O—, —NH—, —C(O)—, and —S—, and each $R_{60}$ is independently selected from hydrogen, $C_1$–$C_8$ alkyl, aryl, $C_1$–$C_8$ alkaryl, $C_1$–$C_8$ alkoxy, aralkyl, and halo. Most preferred are compounds where the N-hydroxyfunctional amide linker, -($L_h$)-, for $R_6$ is selected from the specific groups;

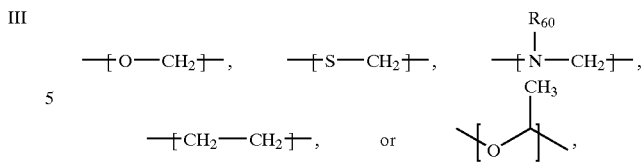

where $R_{60}$ is hydrogen or $C_1$–$C_8$ alkyl.

Preferred as the (N-hydroxyfunctional amide group) in the group $R_6$ is the group:

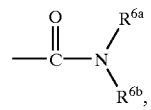

wherein $R^{6a}$ is selected from the group consisting of OH, ($C_1$–$C_6$)alkyl, ($C_1$–$C_6$)alkoxy, heteroaryl and aryl; and wherein $R^{6b}$ is $R^7$ is selected from hydrogen, a non-interfering substituent, or the group, -(La)-(acidic group); wherein -(La)-, is an acid linker having an acid linker length of 1 to 8.

The Acylamino Acid Tetracyclic Compounds of the Invention

The tetracyclic acylamino acid compounds of the invention have the general formula (IV) or a pharmaceutically acceptable salt, solvate or prodrug thereof;

(IV)

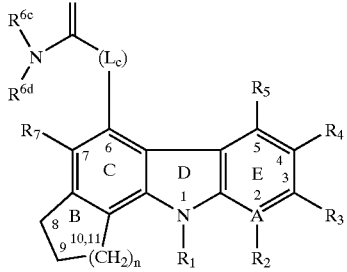

wherein, A is carbon or nitrogen;

$R_1$, $R_2$, $R_3$, and $R_4$ are as described previously;

$R_5$ is -($L_5$)-Z, where -($L_5$)- is a divalent linker group selected from a bond or a divalent group selected from:

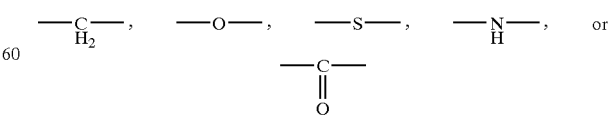

and Z is selected from an amide, thioamide or glyoxylamide, acetamide or thioacetamide, oxime, hydrazide radical (group) represented by the formulae,

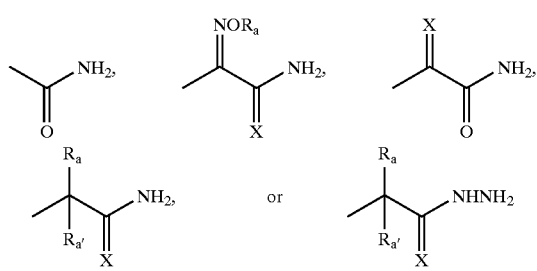

wherein, X is oxygen or sulfur, $R_a$ and $R_{a'}$ are independently selected from hydrogen, $C_1$–$C_8$ alkyl, aryl, $C_1$–$C_8$ alkaryl;

Preferred $R_6$ Substituents:

A preferred subclass of compounds of formula (IV) are those wherein $R_6$ is a substituent having an acylamino acid linker with an acylamino acid linker length of 2 or 3 and the acylamino acid linker group, -($L_c$)-, for $R_6$ is selected from a group represented by the formula;

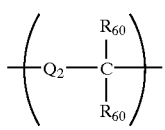

where $Q_2$ is selected from the group —($CH_2$)—, —O—, —NH—, —C(O)—, and —S—, and each $R_{60}$ is independently selected from hydrogen, $C_1$–$C_8$ alkyl, aryl, $C_1$–$C_8$ alkaryl, $C_1$–$C_8$ alkoxy, aralkyl, and halo. Most preferred are compounds where the acylamino acid linker, -($L_c$)-, for $R_6$ is selected from the specific groups;

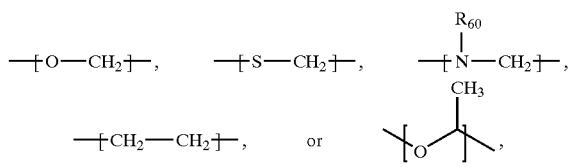

where $R_{60}$ is hydrogen or $C_1$–$C_8$ alkyl.

Preferred as the acylamino acid group in the group $R_6$ is the group:

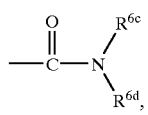

wherein $R^{6c}$ is selected from the group consisting of H, ($C_1$–$C_6$)alkyl, ($C_1$–$C_6$)alkoxy, heteroaryl and aryl; and wherein $NR^{6d}$ is an amino acid residue of either a natural or unnatural amino acid with the nitrogen atom being part of the amino group of the amino acid. A preferred $R^{6c}$ group is the group hydrogen (H). A preferred source of amino acid residue is the amino acid group selected from the group comprising isoleucine, valine, phenylalanine, aspartic acid, leucine, glycine and isomers and derivatives thereof. A salt or a prodrug derivative of the (acylamino acid group) is also a suitable substituent.

Particularly preferred are $R^{6d}$ groups that combine with the nitrogen atom to represent amino acid residues from the amino acid groups selected from: glycine, glycine methyl ester, L-alanine, L-alanine methylester, L-leucine, L-leucine methyl ester, L-aspartic acid, L-aspartic acid dimethylester, L-phenyl alanine, L-phenylalanine methyl ester, aminomalonic acid, aminomalonic acid dimethylester, L-valine, L-valine methyl ester, L-isoleucine, L-isoleucine methyl ester, or salt, and derivatives thereof.

$R_7$ is selected from hydrogen, a non-interfering substituent, or the group, -L($_a$)-(acidic group); wherein -($L_a$)-, is an acid linker having an acid linker length of 1 to 8.

Preferred acylamino acid compounds of the invention are those having the general formula (IVa), or a pharmaceutically acceptable salt, solvate or prodrug derivative thereof;

(IVa)

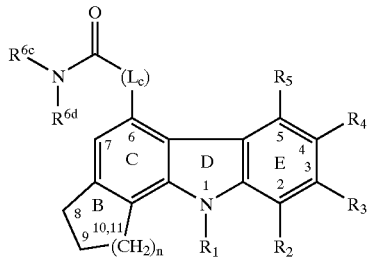

wherein;

the B ring is a cyclopentyl, cyclohexyl or phenyl ring (i.e. combines with the C ring to form naphthalenyl) group with the appropriate number of hydrogen and/or non interfering groups appended;

$R_1$ is selected from $C_1$–$C_8$ alkyl, aryl, and alkylaryl;

$R_2$, $R_3$, and $R_4$ are each independently selected from the group consisting of hydrogen, methyl, ethyl, propyl, isopropyl, cyclopropyl, —F, —$CF_3$, —Cl, —Br, or —O—$CH_3$;

$R_5$ is the group -($L_5$)-Z, wherein Z is selected from the groups amide and hydrazide and wherein $L_5$ is a bond;

and wherein $R^{6c}$ is selected from the group consisting of H, ($C_1$–$C_6$)alkyl, ($C_1$–$C_6$)alkoxy, heteroaryl and aryl; and wherein $NR^{6d}$ is an amino acid residue of either a natural or unnatural amino acid with the nitrogen atom being part of the amino group of the amino acid. A preferred $R^{6c}$ group is the group hydrogen (H); and -(Lc)- is a divalent group selected from;

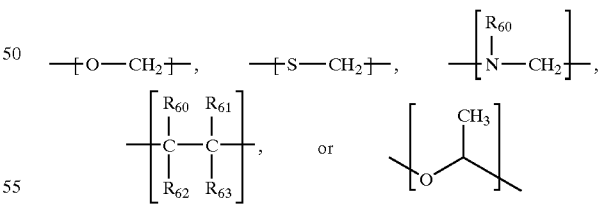

where $R_{60}$, $R_{61}$, $R_{62}$, and $R_{63}$ are each independently selected from hydrogen or $C_1$–$C_8$ alkyl.

The Tetracyclic-5-acetamide sPLA$_2$ Inhibitor Compounds

The tetracyclic-5-acetamide sPLA$_2$ inhibitor compounds of the present invention are represented by compounds of formula (V), and pharmaceutically acceptable salts and prodrug derivatives thereof,

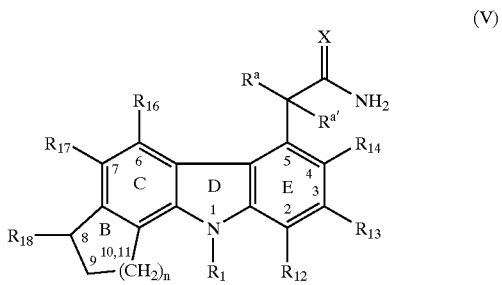

(V)

wherein;

the B ring is a cyclopentyl, cyclohexyl or phenyl ring (i.e. combines with the C ring to form naphthalenyl) group with the appropriate number of hydrogen and/or non interfering groups appended;

X is oxygen, or sulfur;

$R_{12}$, $R_{13}$, and $R_{14}$ are independently selected from the group consisting of is halo, $C_1$–$C_2$ alkylthio, or $C_1$–$C_2$ alkoxy;

each $R_a$ and $R_{a'}$ are as described previously;

$R_{16}$ is the group, -($L_h$)-(N-hydroxyfunctional amide group); wherein -($L_h$)-, is an N-hydroxyfunctional amide linker having an N-hydroxyfunctional amide linker length of 1 to 8; and wherein a N-hydroxyfunctional amide is represented by the formula:

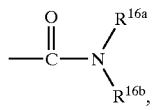

wherein $R^{16a}$ is selected from the group consisting of OH, ($C_1$–$C_6$)alkoxy, and aryloxy; and wherein $R^{16b}$ is hydrogen or an organic substituent selected from the group consisting of $C_1$–$C_8$ alkyl, aryl, $C_7$–$C_{14}$ aralkyl, $C_7$–$C_{14}$ alkaryl, $C_3$–$C_8$ cycloalkyl, $C_1$–$C_8$ alkoxyalkyl and these groups substituted with halogen, —$CF_3$, —OH, $C_1$–$C_8$ alkyl, amino, carbonyl, and —CN; or $R_{16}$ is the group, -($L_c$)-(acylamino acid group); wherein -($L_c$)-, is an acylamino acid linker having an acylamino acid linker length of 1 to 8; or $R_{16}$ is the group, -$L(_a)$-(acidic group); wherein -$L(_a)$-, is an acid linker having an acid linker length of 1 to 8;

$R_{17}$ and $R_{18}$ are each independently hydrogen, $C_1$–$C_{10}$ alkyl, $C_1$–$C_{10}$ alkenyl, $C_1$–$C_{10}$ alkynyl, $C_3$–$C_8$ cycloalkyl, aryl, aralkyl, or any two adjacent hydrocarbyl groups in the set $R_{16}$, $R_{17}$, and $R_{18}$, combine with the ring carbon atoms to which they are attached to form a 5- or 6-membered substituted or unsubstituted carbocyclic ring; or $C_1$–$C_{10}$ haloalkyl, $C_1$–$C_{10}$ alkoxy, $C_1$–$C_{10}$ haloalkoxy, $C_4$–$C_8$ cycloalkoxy, phenoxy, halo, hydroxy, carboxyl, —SH, —CN, $C_1$–$C_{10}$ alkylthio, arylthio, thioacetal, —C(O)O($C_1$–$C_{10}$) alkyl, hydrazide, hydrazino, hydrazido, —$NH_2$, —$NO_2$, —$NR_{82}R_{83}$, and —C(O)$NR_{82}R_{83}$, where, $R_{82}$ and $R_{83}$ are independently hydrogen, $C_1$–$C_{10}$ alkyl, $C_1$–$C_{10}$ hydroxyalkyl, or taken together with N, $R_{82}$ and $R_{83}$ form a 5- to 8-membered heterocyclic ring; or a group having the formula;

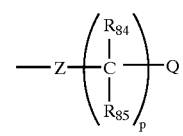

where, $R_{84}$ and $R_{85}$ are each independently selected from hydrogen, $C_1$–$C_{10}$ alkyl, hydroxy, or $R_{84}$ and $R_{85}$ taken together are =O;

p is 1 to 5,

Z is a bond, —O—, —N($C_1$–$C_{10}$ alkyl)-, —NH—, or —S—; and

Q is —CON($R_{82}R_{83}$), -5-tetrazolyl, —$SO_3H$,

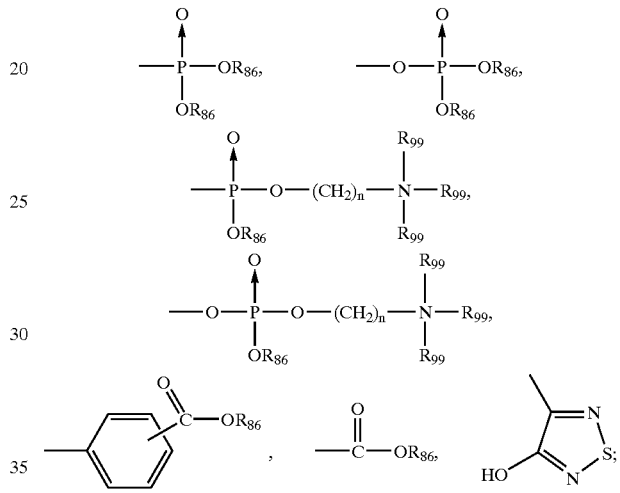

where n is 1 to 8, $R_{86}$ is independently selected from hydrogen, a metal, or $C_1$–$C_{10}$ alkyl, and $R_{99}$ is selected from hydrogen or $C_1$–$C_{10}$ alkyl.

The Tetracyclic-5-amide Compounds

A compound of formula (VI) or a pharmaceutically acceptable salt, solvate or prodrug is representative of tetracyclic-5-amide compounds of the invention thereof;

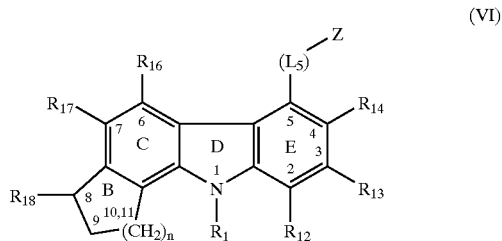

(VI)

wherein;

the B ring is a cyclopentyl, cyclohexyl or phenyl ring (i.e. combines with the C ring to form naphthalenyl) group with the appropriate number of hydrogen and/or non interfering groups appended;

$R_1$ is as described previously $R_{12}$ is hydrogen, or a group containing 1 to 4 non-hydrogen atoms plus any required hydrogen atoms;

$R_{13}$ and $R_{14}$ are independently hydrogen or a non-interfering group;

-($L_5$)-Z, is the group where -($L_5$)- is a divalent linker group selected from a bond or a divalent group selected from:

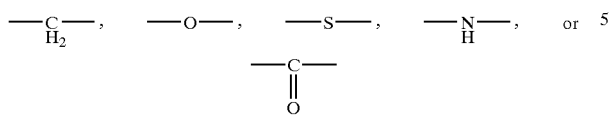

and z is selected from an amide or thioamide radical or a group represented by the formulae,

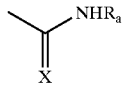

wherein, X is oxygen or sulfur; and $R_a$ is selected from hydrogen, $C_1$–$C_8$ alkyl, aryl, $C_1$–$C_8$ alkaryl;

$R_{16}$ is the group, -L($_a$)-(acidic group); wherein -L($_a$)-, is an acid linker having an acid linker length of 1 to 8, or the group -($L_h$)-(N-hydroxyfunctional amide group); wherein -($L_h$)-, is an N-hydroxyfunctional amide linker having an N-hydroxyfunctional amide linker length of 1 to 8; or the group -($L_c$)-(acylamino acid group); wherein -($L_c$)- is an acylamino acid linker having an acylamino acid linker length of 1 to 8.

$R_{17}$ is selected from hydrogen, a non-interfering substituent, or the group, -L($_a$)-(acidic group); wherein -L($_a$)-, is an acid linker having an acid linker length of 1 to 8; or $R_{17}$ is selected from hydrogen, non-interfering substituent, carbocyclic radical, carbocyclic radical substituted with non-interfering substituent(s), heterocyclic radicals, and heterocyclic radical substituted with non-interfering substituent(s).

$R_{18}$ is selected from hydrogen, non-interfering substituent, carbocyclic radical, carbocyclic radical substituted with non-interfering substituent(s), heterocyclic radicals, and heterocyclic radical substituted with non-interfering substituent(s).

The Tetracyclic-5-glyoxylamide Compounds

Compounds of formula (VII) or a pharmaceutically acceptable salt, solvate or prodrug represent tetracyclic-5-glyoxylamide compounds of the invention thereof;

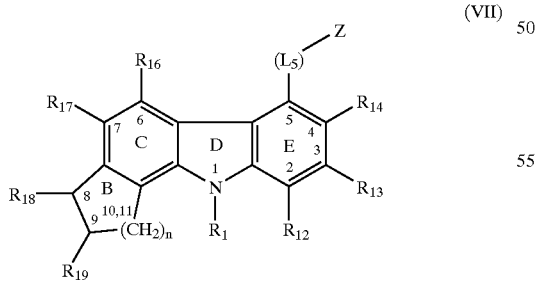

(VII)

wherein;

$R_1$ is as described previously;

$R_{12}$ is hydrogen, or a group containing 1 to 4 non-hydrogen atoms plus any required hydrogen atoms;

$R_{13}$ and $R_{14}$ are independently selected from hydrogen or a non-interfering group;

$R_{15}$ is -($L_5$)-Z, where -($L_5$)- is a divalent linker group selected from a bond or a divalent group selected from:

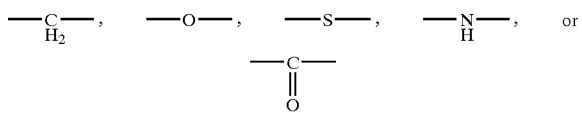

and Z is a glyoxylamide group represented by the formulae,

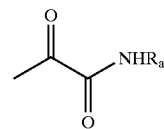

wherein, $R_a$ is selected from hydrogen, ($C_1$–$C_8$)alkyl, aryl, ($C_1$–$C_8$)alkaryl, and aralkyl; and wherein $R_a$ is hydrogen is most preferred;

$R_{16}$ is the group, -L($_a$)-(acidic group); wherein -L($_a$)-, is an acid linker having an acid linker length of 1 to 8, or the group -($L_h$)-(N-hydroxyfunctional amide group); wherein -($L_h$)-, is an N-hydroxyfunctional amide linker having an N-hydroxyfunctional amide linker length of 1 to 8; or the group -($L_c$)-acylamino acid group); wherein -($L_c$)-, is an acylamino acid linker having an acylamino acid linker length of 1 to 8;

$R_{17}$ is selected from hydrogen, a non-interfering substituent, or the group, -L($_a$)-(acidic group); wherein -L($_a$)-, is an acid linker having an acid linker length of 1 to 8;

$R_{18}$ and $R_{19}$ are independently selected from hydrogen, non-interfering substituent, carbocyclic radical, carbocyclic radical substituted with non-interfering substituent(s), heterocyclic radicals, and heterocyclic radical substituted with non-interfering substituent(s).

The Tetracyclic-5-oxime Amide Compounds

Tetracyclic 5-oxime amide compounds of the present invention or a pharmaceutically acceptable salt, solvate or prodrug derivatives thereof are also compounds of the present invention and are useful for the treatment and/or prophylaxis of inflammation and inflammatory diseases. Tetracyclic 5-oxime amide compounds of the invention are represented by the formula (VIII):

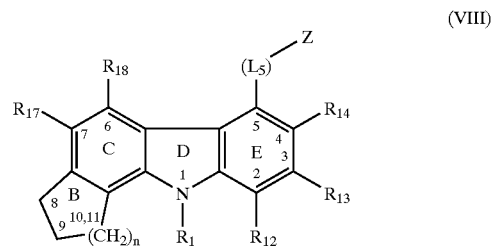

(VIII)

wherein;

the B ring is a cyclopentyl, cyclohexyl or phenyl ring (i.e. combines with the C ring to form naphthalenyl) group with the appropriate number of hydrogen and/or non interfering groups appended;

$R_1$ is as described previously;

$R_{12}$ is hydrogen, or a group containing 1 to 4 non-hydrogen atoms plus any required hydrogen atoms;

$R_{13}$ and $R_{14}$ are each independently a non-interfering group;

-($L_5$)-Z, is the group where -($L_5$)- is a divalent linker group selected from a bond or a divalent group selected from:

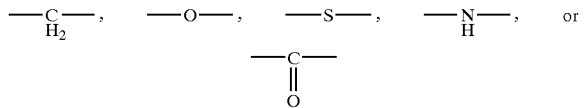

and Z is selected from an oxime amide group represented by the formulae,

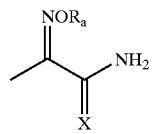

wherein, X is oxygen or sulfur; and $R_a$ is selected from hydrogen, $C_1$–$C_8$ alkyl, aryl, $C_1$–$C_8$ alkaryl, $C_1$–$C_8$ alkoxy, aralkyl and —CN;

$R_{16}$ is the group, hydrogen, or the group -L($_a$)- (acidic group); wherein -L($_a$)-, is an acid linker having an acid linker length of 1 to 8, or the group -($L_h$)-(N-hydroxyfunctional amide group); wherein -($L_h$)-, is an N-hydroxyfunctional amide linker having an N-hydroxyfunctional amide linker length of 1 to 8; or the group -($L_c$)-(acylamino acid group); wherein -($L_c$)- is acylamino acid linker having an acylamino acid linker length of 1 to 8;

$R_{17}$ is selected from hydrogen, a non-interfering substituent, or the group, -L($_a$)-(acidic group); wherein -L($_a$)-, is an acid linker having an acid linker length of 1 to 8.

$R_{18}$, and $R_{19}$ are selected from hydrogen, non-interfering substituent, carbocyclic radical, carbocyclic radical substituted with non-interfering substituent(s), heterocyclic radicals, and heterocyclic radical substituted with non-interfering substituent(s).

Most preferred compounds (and all pharmaceutically acceptable salts, solvates and prodrug derivatives thereof) which are illustrative of the compounds of the invention for treatment of a human afflicted with Inflammatory Disease, a pharmaceutically acceptable salt, solvate, or a prodrug derivative of a compound selected from the group consisting of:

(10-Benzyl-6-carbamoyl-1,2,3,10-tetraydrocyclopenta[a]carbazol-5-yloxy)acetic acid methyl ester,
(10-Benzyl-6-carbamoyl-1,2,3,10-tetraydrocyclopenta[a]carbazol-5-yloxy)acetic acid,
(10-Benzyl-6-carbamoyl-1,2,3,10-tetraydrocyclopenta[a]carbazol-5-yloxy)acetic acid methyl ester,
10-Benzyl-6-carbamoyl-1,2,3,10-tetraydrocyclopenta[a]carbazol-5-yloxy)acetic acid,
(11-Benzyl-7-carbamoyl-2,3,4,11-tetraydro-1H-benzo[a]carbazol-6-yloxy)acetic acid methyl ester, and
(11-Benzyl-7-carbamoyl-2,3,4,11-tetraydro-1H-benzo[a]carbazol-6-yloxy)acetic acid.

represented by the formulae (C1), (C2), (C3), (C4), (C5), (C6), (C7), (C8), or (C9);

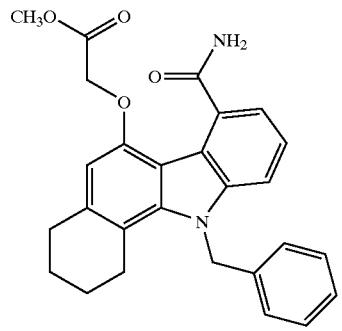
(C1)

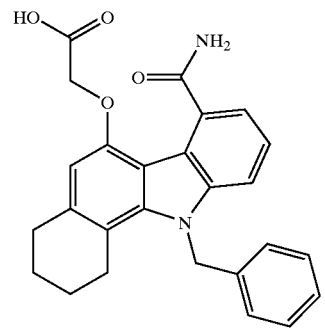
(C2)

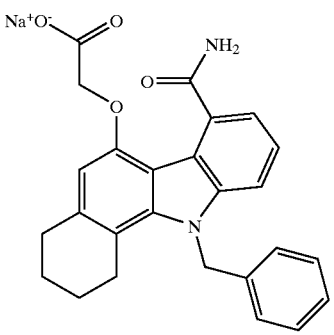
(C3)

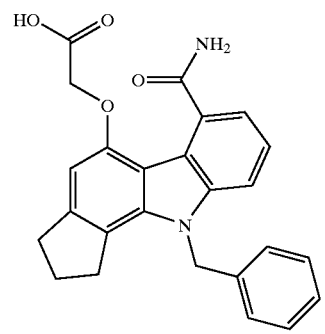
(C4)

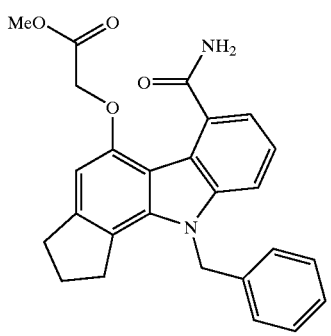
(C5)

(C6) 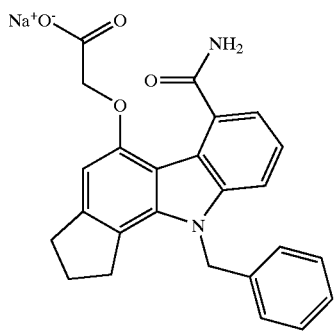

(C7) 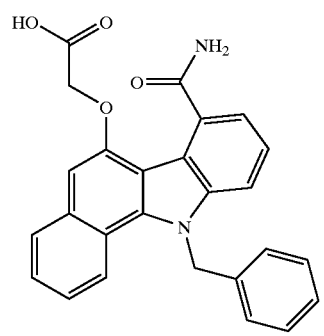

(C8) 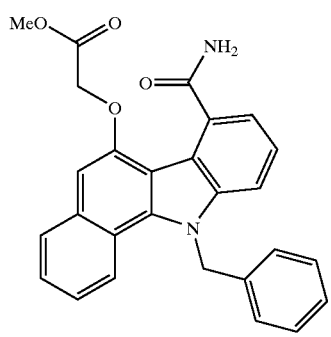

(C9) 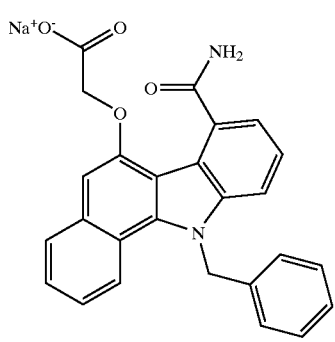

Particularly preferred is a tetracyclic compound represented by the formula (II') or a pharmaceutically acceptable salt, solvate, or prodrug derivative thereof;

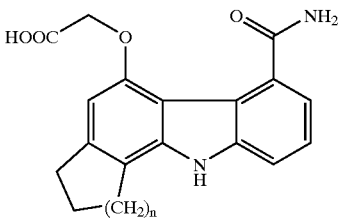 (II')

wherein;

n is 1 or 2;

Also particularly preferred is a tetracyclic compound represented by the formula (II") or a pharmaceutically acceptable salt, solvate, or prodrug derivative thereof;

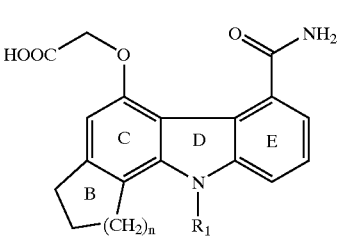 (II")

wherein;

n is 2 and B ring is fully unsaturated (i.e. B+C ring= naphthyl); and $R_1$ is as described previously.

The salts of the above tetracyclic compounds represented by formulae (I), (II), (III), (IV), (V), (VI), (VII), and (VIII) are an additional aspect of the invention.

In those instances when the compound of the invention possesses acidic or basic functional groups, various salts may be formed which are more water soluble and more physiologically suitable than the parent compound.

Representative pharmaceutically acceptable salts, include but are not limited to, the alkali and alkaline earth salts such as lithium, sodium, potassium, calcium, magnesium, aluminum and the like. Salts are conveniently prepared from the free acid by treating the acid in solution with a base or by exposing the acid to an ion exchange resin.

Included within the definition of pharmaceutically acceptable salts are the relatively non-toxic, inorganic and organic base addition salts of compounds of the present invention, for example, ammonium, quaternary ammonium, and amine cations, derived from nitrogenous bases of sufficient basicity to form salts with the compounds of this invention (see, for example, S. M. Berge, et al., "Pharmaceutical Salts," *J. Phar. Sci.*, 66: 1–19 (1977)). Moreover, the basic group(s) of the compound of the invention may be reacted with suitable organic or inorganic acids to form salts such as acetate, benzenesulfonate, benzoate, bicarbonate, bisulfate, bitartrate, borate, bromide, camsylate, carbonate, chloride, clavulanate, citrate, chloride, edetate, edisylate, estolate, esylate, fluoride, fumarate, gluceptate, gluconate, glutamate, glycolylarsanilate, hexylresorcinate, bromide, chloride, hydroxynaphthoate, iodide, isothionate, lactate, lactobionate, laurate, malate, malseate, mandelate, mesylate, methylbromide, methylnitrate, methylsulfate, mucate, napsylate, nitrate, oleate, oxalate, palmitate, pantothenate, phosphate, polygalacturonate, salicylate, stearate, subacetate, succinate, tannate, tartrate, tosylate, trifluoroacetate, trifluoromethane sulfonate, and valerate.

Certain compounds of the invention may possess one or more chiral centers, and thus, may exist in optically active forms. Likewise, when the compounds contain an alkenyl or alkenylene group, there exist the possibility of cis- and trans-isomeric forms of the compounds. The R- and S-isomers and mixtures thereof, including racemic mixtures as well as mixtures of cis- and trans-isomers, are contemplated by this invention. Additional asymmetric carbon atoms can be present in a substituent group such as an alkyl group. All such isomers as well as the mixtures thereof are intended to be included in the invention. If a particular stereoisomer is desired, it can be prepared by methods well known in the art by using stereospecific reactions with starting materials which contain the asymmetric centers and are already resolved or, alternatively by methods which lead to mixtures of the stereoisomers and subsequent resolution by known methods. For example, a racemic mixture may be reacted with a single enantiomer of some other compound. This changes the racemic form into a mixture of stereoisomers and diastereomers, because they have different melting points, different boiling points, and different solubilities and can be separated by conventional means, such as crystallization.

Prodrugs are derivatives of the compounds of the invention which have chemically or metabolically cleavable groups and become by solvolysis or under physiological conditions the compounds of the invention which are pharmaceutically active in vivo. Derivatives of the compounds of this invention have activity in both their acid and base derivative forms, but the acid derivative form often offers advantages of solubility, tissue compatibility, or delayed release in a mammalian organism (see, Bundgard, H., *Design of Prodrugs*, pp. 7–9, 21–24, Elsevier, Amsterdam 1985). Prodrugs include acid derivatives well known to practitioners of the art, such as, for example, esters prepared by reaction of the parent acidic compound with a suitable alcohol, or amides prepared by reaction of the parent acid compound with a suitable amine. Simple aliphatic or aromatic esters derived from acidic groups pendent on the compounds of this invention are preferred prodrugs. In some cases it is desirable to prepare double ester type prodrugs such as (acyloxy)alkyl esters or ((alkoxycarbonyl)oxy)alkyl esters. Particularly preferred esters as prodrugs are methyl, ethyl, propyl, isopropyl, n-butyl, isobutyl, tert-butyl, morpholinoethyl, and N,N-diethylglycolamido.

N,N-diethylglycolamido ester prodrugs may be prepared by reaction of the sodium salt of a compound of Formula (I) (in a medium such as dimethylformamide) with 2-chloro-N,N-diethylacetamide (available from Aldrich Chemical Co., Milwaukee, Wis. USA; Item No. 25,099-6). Morpholinylethyl ester prodrugs may be prepared by reaction of the sodium salt of a compound of formula (I) (in a medium such as dimethylformamide) with 4-(2-chloroethyl)morpholine hydrochloride (available from Aldrich Chemical Co., Milwaukee, Wis. USA, Item No. C4, 220-3).

(III) Method of Preparing the Tetracyclic-5-amide Compound

The tetracyclic-5-amide compounds are compounds of this invention and are also useful as intermediates or starting materials for preparing other compounds of the invention.

The tetracyclic-5-amide compounds are prepared by following a scheme such as Scheme 1, as shown below:

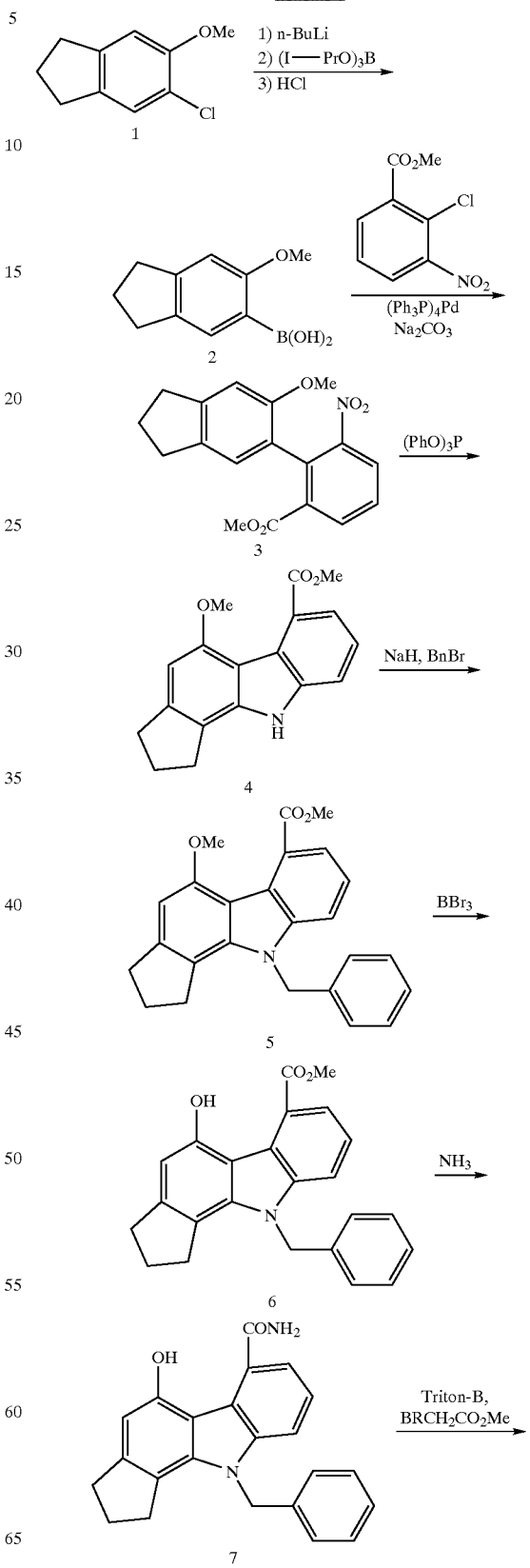

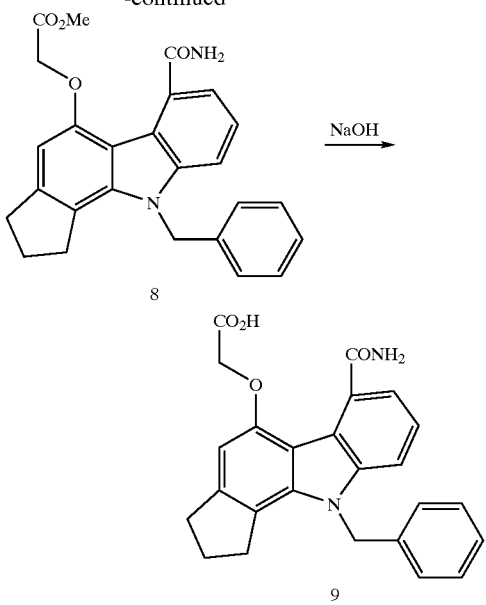

Scheme 1 depicts a protocol for preparing compounds of the invention wherein the B ring is a cyclopentane ring system. By use of indanes substituted on the cyclopentane ring, substituted analogs of compounds of the invention as described, may be prepared. As shown, the reaction of 5-halo-6-methoxy indane, wherein halo is preferably iodo, bromo or chloro, more preferably bromo, with n-butyl lithium or similar organolithium reagent affords 5-lithio-6-methoxy indane intermediate. Addition of a borate ester e.g., triisopropyl borate to the 5-lithio-6-methoxy indane intermediate generates the corresponding boronic acid compound (2) upon acidic work-up with for example, aqueous HCl. The boronic acid compound (2) is then coupled with methyl-2-halo-3-nitrobenzoate (preferably chloro analog i.e., methyl-2-chloro-3-nitrobenzoate) in a Suzuki type coupling reaction (*Synth. Commun.*, 11, 513 (1981)). The reaction involves use of tetrakis(triphenylphosphine)palladium (0) or other suitable palladium catalyst, and a base such as sodium carbonate. Upon work-up and isolation, i.e., by chromatography, the coupling reaction product (3) is obtained. One of skill in the art is aware that substituted analogs of the compound (3) may be prepared by using methyl-2-halo-3-nitro benzoate reagents with non-interfering substituents at the 4-, 5- and/or 6-position(s) of the benzene ring. The compound (3) is reductively cyclized to the carbazole type tetracyclic compound of (4) using a molar equivalent to excess triphenyl phopsphite under sealed tube conditions. The reductive cyclization reaction for converting compound (3) to compound (4) is performed at temperatures of about 100° C. to 180° C., preferably about 160° C. ("The Reactivity of Organophosphorus Compounds. Part XIX. Reduction of Nitro-compounds by Triethyl Phosphite: a Convenient New Route to Carbazoles, Indoles, Indazoles, Triazoles, and Related Compounds," J. I. G. Cadogan, M. Cameron-Wood, R. K. Mackie, and R. J. G. Searle, *J. Chem. Soc.*, 1965, 4831.). The compound (4) is alkylated or arylated at the carbazole nitrogen to introduce the $R_1$ group by a base catalyzed deprotonation, followed by a nucleophilic attack on an electrophile. Electrophilic groups suitable for this reaction are those necessary to incorporate the $R_1$ group described previously and include for example, alkyl, aryl, and arylalkyl groups as the halides, sulfonates or other leaving groups. For example the reaction of compound (4) with sodium hydride or other suitable base (i.e. n-BuLi, lithiumdiisopropylamide, etc.) is performed in a suitable solvent, e.g., dimethylformamide at temperatures ranging from −78° C. to about 25° C. depending on the base and solvent, and preferably in an inert solvent. This is followed by addition of benzyl bromide for example, to afford upon work-up the compound of formula (5) or analog thereof. The compound (5) is de-methylated by reaction with boron tribromide or sodium thioethoxide in a suitable solvent such as dichloromethane. About 1.0 to 2.0 equivalents of boron tribromide is typically sufficient to effect complete reaction. The de-methylation reaction temperature is from about −12° C. to about 10° C. Work-up is effected by stirring with methyl alcohol, followed by neutralization with a base e.g. sodium bicarbonate, with subsequent extraction and purification to afford compound (6).

A solution of compound (6) or analog thereof, in THF is reacted with condensed ammonia in a sealed tube from about 20° C. to about 70° C. preferably at about 50° C., over a period of 1 to 7 days, preferably 4 days. Condensed ammonia is obtained by running a stream of ammonia gas over the solution at about −78° C. as desired. Alternatively, the reaction can be performed by directly heating a mixture of excess ammonia gas and compound (6) in a sealed tube under temperature and time conditions as described above, to afford the compound (7).

The compound (7) is then subjected to an alkylation reaction with 2-bromomethylacetate using a basic catalyst such as benzyltrimethylammonium hydroxide Triton-B, Rohm and Haas Corporation trademark), or cesium carbonate or the like to afford the compound (8) or analog thereof based on starting material.

The compound of formula (8), itself a compound of the invention, may be converted to the free acid or acid salt. The free acid compound (9) is obtained by reaction with sodium hydroxide (saponification) or lithium hydroxide in a suitable solvent, e.g., THF, followed by acidic work-up, e.g. with HCl to afford the free acid compound (9). Alternatively, the salt, e.g., the sodium salt, could be isolated by foregoing the acid wash step.

Compounds of formula I or intermediates thereto, wherein the B ring is a cyclohexyl or a substituted cylcohexane ring are prepared by starting with 6-methoxy-5-halo-1,2,3,8 tetrahydronaphthalene or analog substituted with non-interfering groups. The protocol according to Scheme 2 below;

Scheme 2

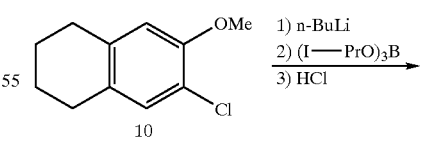

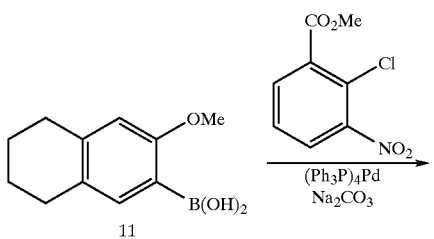

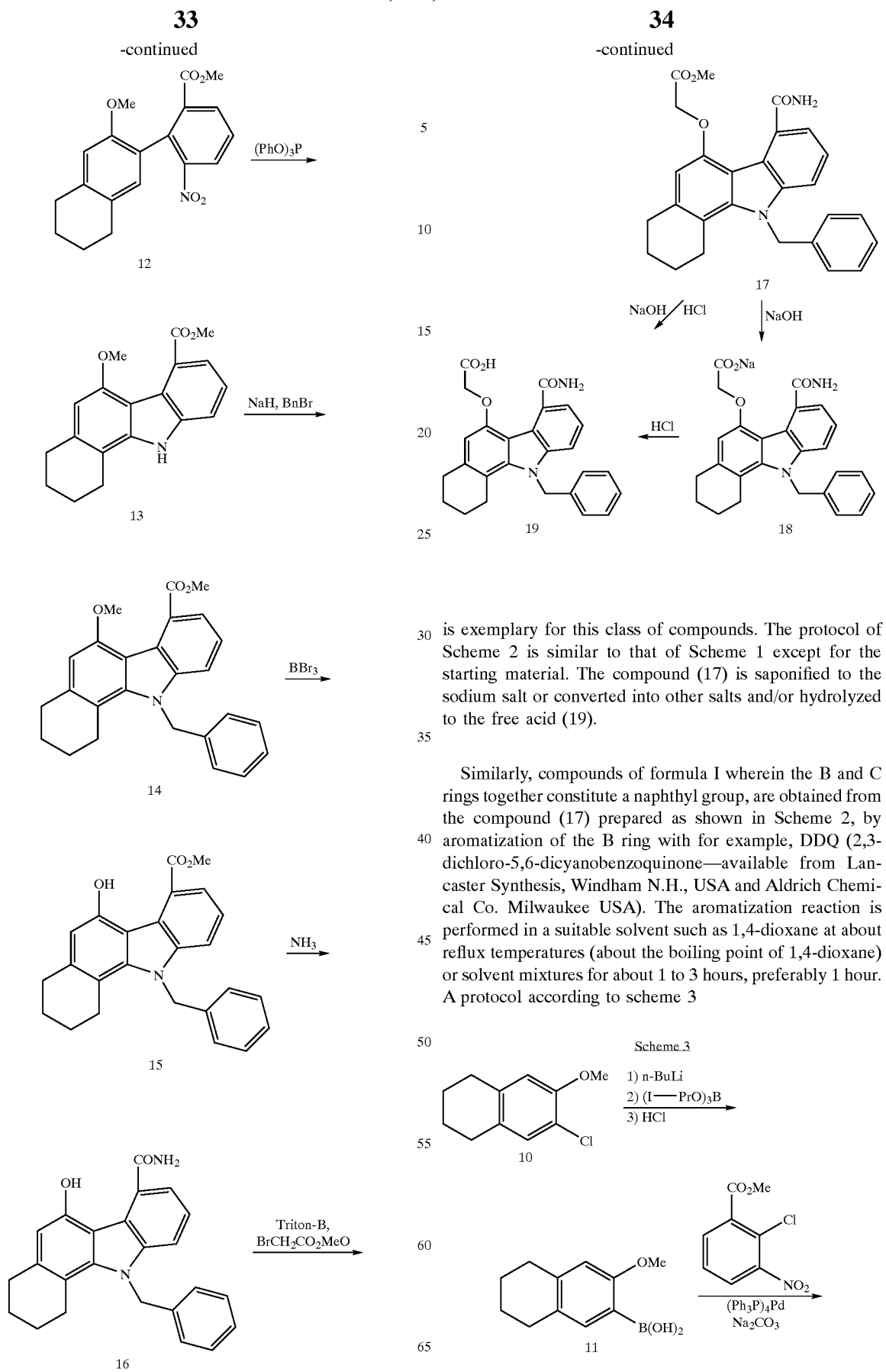

is exemplary for this class of compounds. The protocol of Scheme 2 is similar to that of Scheme 1 except for the starting material. The compound (17) is saponified to the sodium salt or converted into other salts and/or hydrolyzed to the free acid (19).

Similarly, compounds of formula I wherein the B and C rings together constitute a naphthyl group, are obtained from the compound (17) prepared as shown in Scheme 2, by aromatization of the B ring with for example, DDQ (2,3-dichloro-5,6-dicyanobenzoquinone—available from Lancaster Synthesis, Windham N.H., USA and Aldrich Chemical Co. Milwaukee USA). The aromatization reaction is performed in a suitable solvent such as 1,4-dioxane at about reflux temperatures (about the boiling point of 1,4-dioxane) or solvent mixtures for about 1 to 3 hours, preferably 1 hour. A protocol according to scheme 3

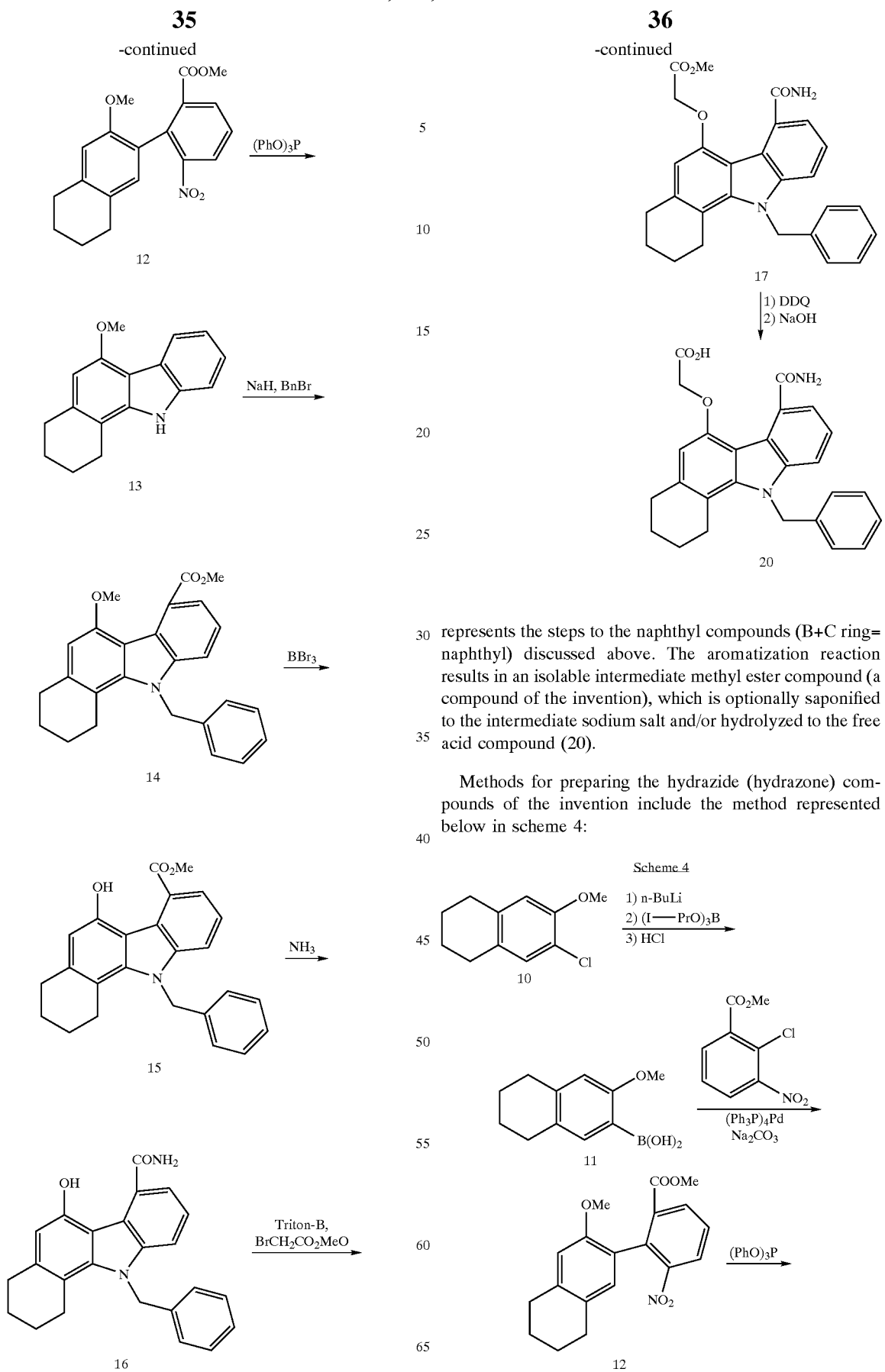

represents the steps to the naphthyl compounds (B+C ring= naphthyl) discussed above. The aromatization reaction results in an isolable intermediate methyl ester compound (a compound of the invention), which is optionally saponified to the intermediate sodium salt and/or hydrolyzed to the free acid compound (20).

Methods for preparing the hydrazide (hydrazone) compounds of the invention include the method represented below in scheme 4:

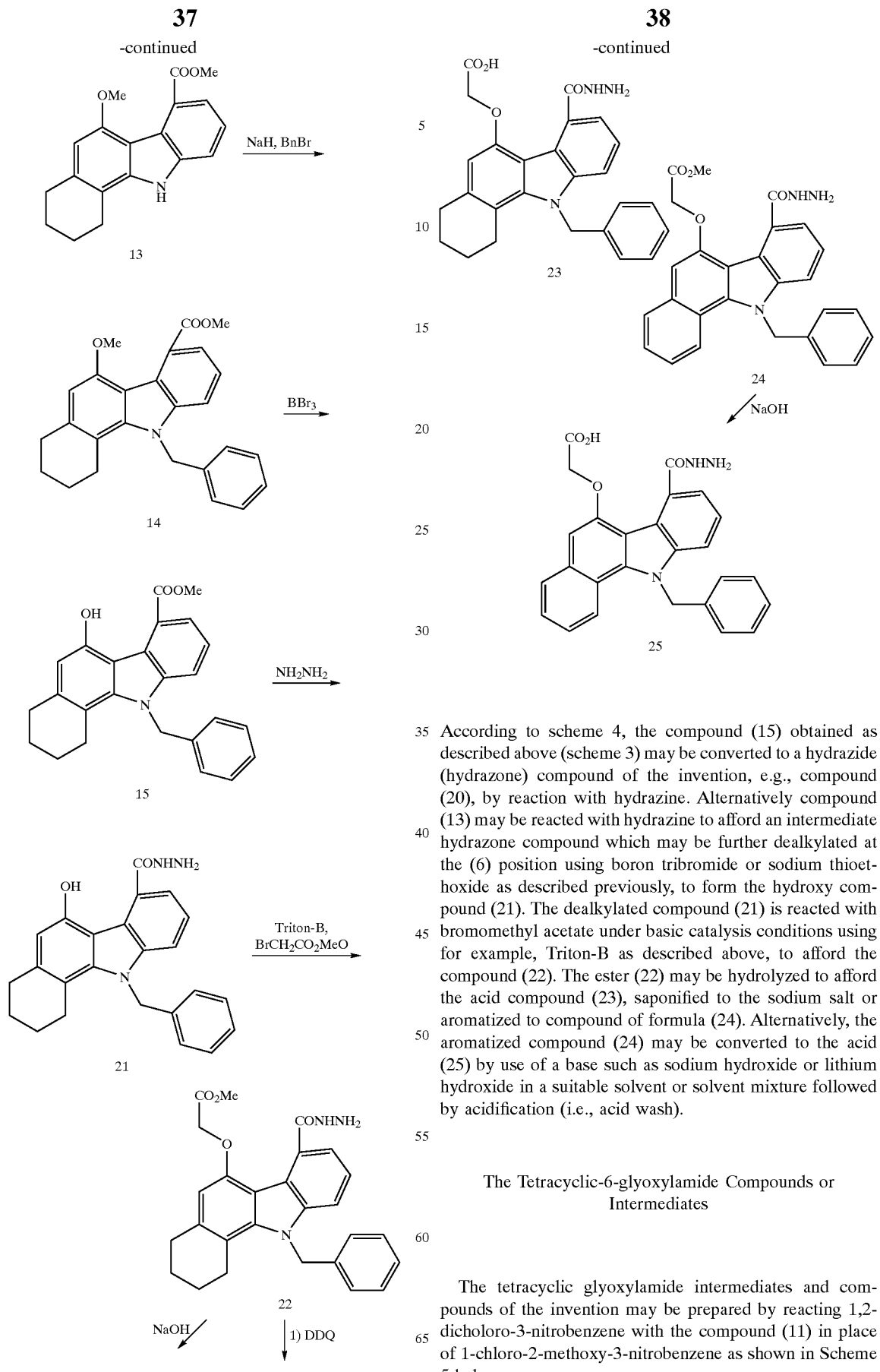

According to scheme 4, the compound (15) obtained as described above (scheme 3) may be converted to a hydrazide (hydrazone) compound of the invention, e.g., compound (20), by reaction with hydrazine. Alternatively compound (13) may be reacted with hydrazine to afford an intermediate hydrazone compound which may be further dealkylated at the (6) position using boron tribromide or sodium thioethoxide as described previously, to form the hydroxy compound (21). The dealkylated compound (21) is reacted with bromomethyl acetate under basic catalysis conditions using for example, Triton-B as described above, to afford the compound (22). The ester (22) may be hydrolyzed to afford the acid compound (23), saponified to the sodium salt or aromatized to compound of formula (24). Alternatively, the aromatized compound (24) may be converted to the acid (25) by use of a base such as sodium hydroxide or lithium hydroxide in a suitable solvent or solvent mixture followed by acidification (i.e., acid wash).

The Tetracyclic-6-glyoxylamide Compounds or Intermediates

The tetracyclic glyoxylamide intermediates and compounds of the invention may be prepared by reacting 1,2-dicholoro-3-nitrobenzene with the compound (11) in place of 1-chloro-2-methoxy-3-nitrobenzene as shown in Scheme 5 below:

Scheme 5
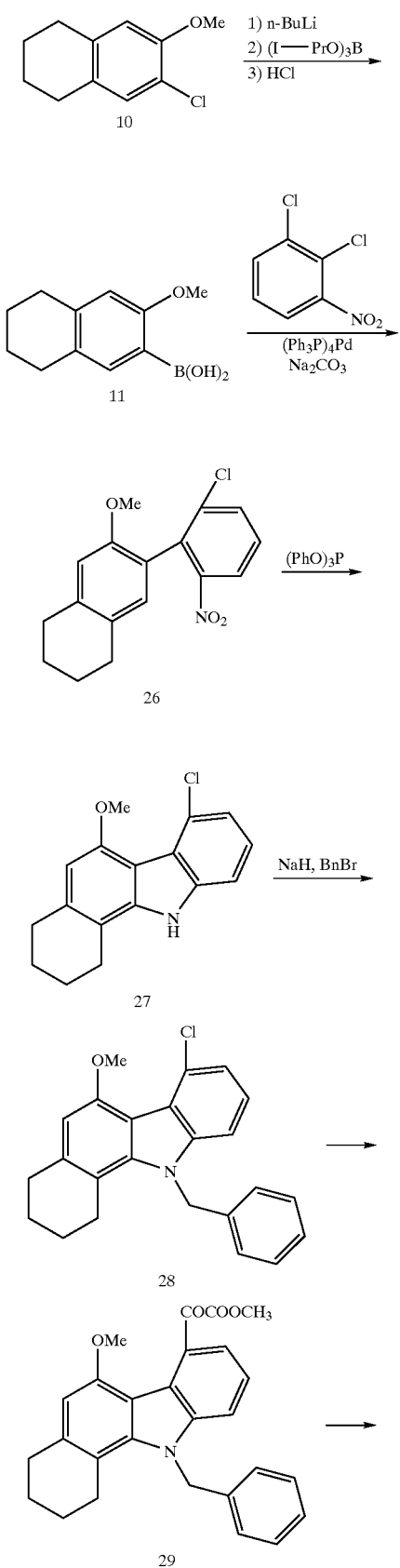
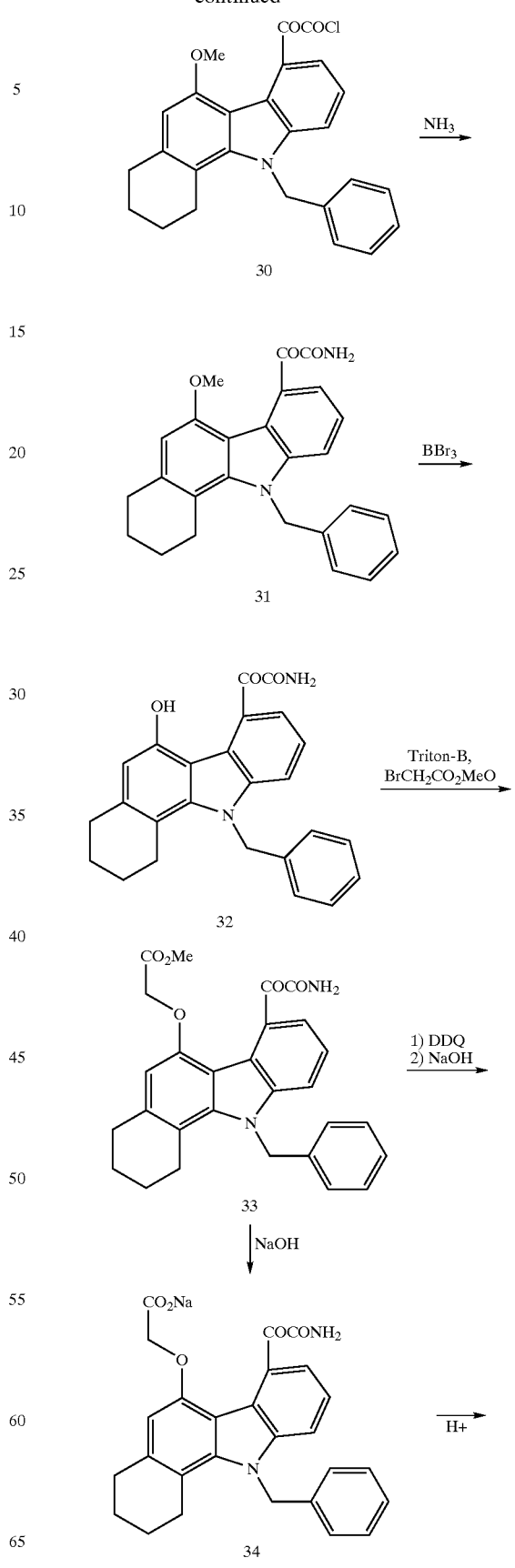

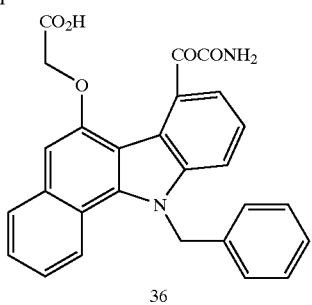

36

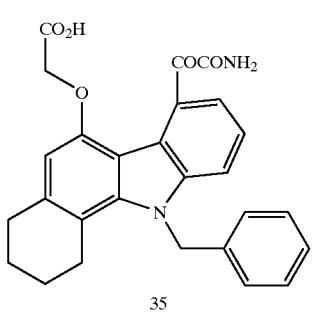

35

Alternatively, 1-chloro-2-bromo-3-nitrobenzene may be reacted with the starting material compound (11). Compound (11) is itself prepared as described in Scheme 2. In either case a mixture of products is possible and the desired product (26) is isolated and purified by chromatography, distillation, crystallization or a combination of these methods. Again, the Suzuki type coupling is employed to afford the compound (26). The compound (26) is reacted with triphenylphosphite as in Scheme (1) or (2) to afford the reductive cyclization product (27). The compound (27) is alkylated at the nitrogen atom by reaction with a molar, or slight excess of NaH in a polar aprotic solvent, such as dimethylformamide, followed by addition of an electrophile source such as for example, benzylbromide, to afford the compound (28). The compound (28) is reacted with n-butyl lithium or other suitable base to afford a metal-halogen exchange reaction, an un-isolated intermediate lithio compound. This is followed by addition of dimethyl oxalate to afford the methyl oxalate compound (29). Reaction of compound (29) with a halogenating agent i.e. anhydrous HCl, thionyl chloride etc., affords the chloride compound (30). The compound (30) is reacted with ammonia condensate (condensation of ammonia gas by cooling to form liquid ammonia as discussed previously) to afford the glyoxylamide compound (31). The ammonation may be accomplished by reacting compound (30) and ammonia in a pressure vessel at about 30 to 80° C. for about 10 minutes to 4 hours, followed by appropriate cooling (i.e. about −78° C.), and isolation of product. Alternatively other methods of functionalizing the oxalyl group may be applied depending on substrate sensitivity. Other methods may include use of reagents for conversion of esters to amides (Larock, supra) or conversion to activated esters followed by use of amide coupling agents (see generally, J. March, Advanced Organic Chemistry, $3^{rd}$ ed., Wiley Intersciences, New York, N.Y.). Compound (31) is then de-methylated at the (6) position (or at the 7-position if starting with a compound that places methoxy group at the 7-position). De-methylation is accomplished by reaction with boron tribromide following a procedure described in the examples to afford the compound (32) having a hydroxyl group at position 6- or 7- as the case may be. The compound (32) may be elaborated to the oxyacetic acid methyl ester derivative (33) by reaction with bromoacetic acid methyl ester (methylbromoacetate) to afford the methyl ester (33). Formation of compound (33) is accomplished in the presence of a basic catalyst such as tetra-n-butylammonium bromide, or Triton-B™ or cesium carbonate. The methyl ester (33) may be saponified to the salt e.g., the sodium salt (34), using sodium hydroxide, or to the potassium salt using potassium hydroxide. Optionally, the salt, e.g., the sodium salt (34), may be converted to the acid (35) using dilute HCl or other suitable acids. The acid (35) may be aromatized to the naphthyl compound (36). Alternatively, the methyl ester (33) may be aromatized to an intermediate naphthyl compound followed by saponification and acidification (i.e., sodium hydroxide treatment followed by acid wash) to the acid (36)

The Tetracyclic-5-acetamide Compounds

The tetracyclic compounds of the present invention having the acetamide group at 5-position may be prepared as shown in scheme 6 below:

Scheme 6

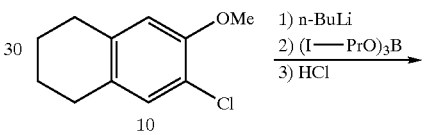

10

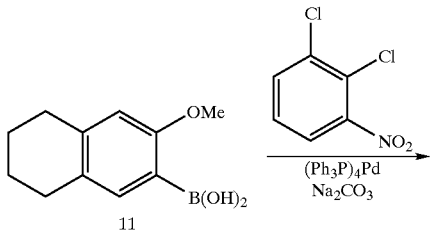

11

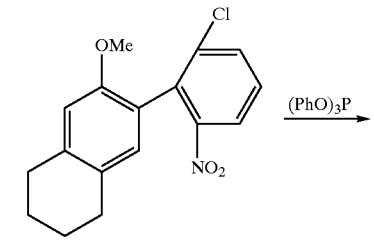

26

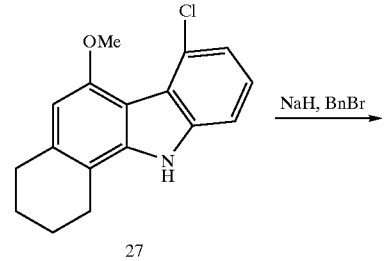

27

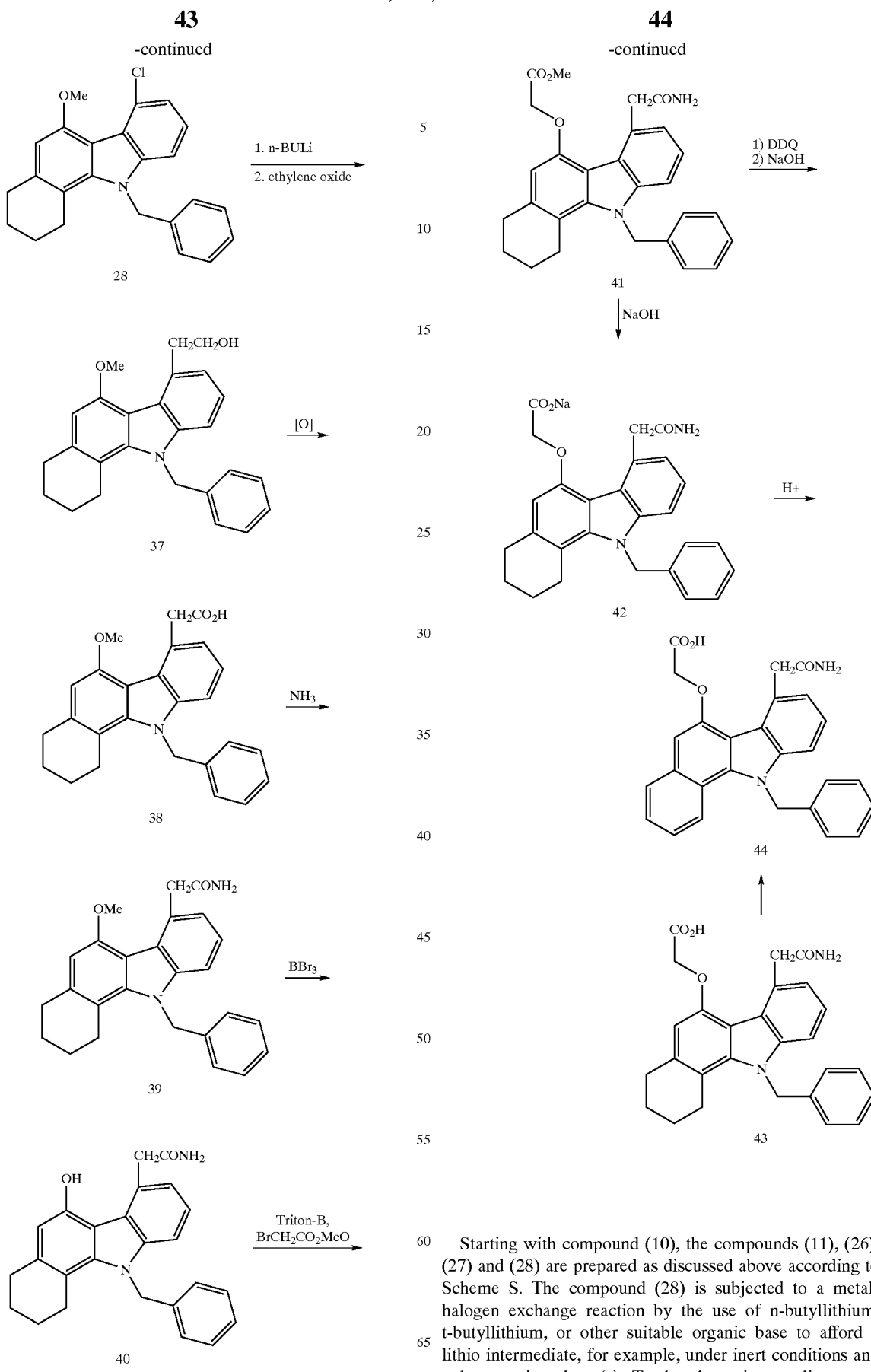

Starting with compound (10), the compounds (11), (26), (27) and (28) are prepared as discussed above according to Scheme S. The compound (28) is subjected to a metal-halogen exchange reaction by the use of n-butyllithium, t-butyllithium, or other suitable organic base to afford a lithio intermediate, for example, under inert conditions and polar aprotic solvent(s). To the above intermediate compound is added a terminal epoxide, e.g., ethylene oxide, to afford the terminal alcohol by a nucleophilic ring opening reaction followed by an aqueous acidic work-up. The terminal alcohol product (37) is isolated preferably by aqueous work-up or by other methods known to one of skill in the art. The terminal alcohol (37) is oxidized to the acid, for example, by use of sodium hypochlorite or other alcohol oxidizing agents. The acid (38) is then converted to the amide, i.e. acetamide (39), by reaction with ammonia as described supra or by use of amide forming reagents and conditions known to one of skill in the art or taught in reference literature such as for example, J. March, Advanced Organic Chemistry (supra), or Larock (supra). The acetamide (39) is then de-methylated with boron tribromide as described previously to afford the hydroxy compound (40). This is followed by elaboration of the hydroxy group of compound (40) to the oxymethyl acetate derivative (41). This is accomplished, for example, by a basic catalysis with methyl bromoacetate and tetra-n-butylammonium bromide (TBAB) or Triton-B™ in methylene chloride. The methyl ester compound (41) may be saponified to the sodium salt (42) followed by conversion to the acid (43) following a procedure described previously. The acid (43) may be aromatized to the naphthyl compound (44).

Alternatively, the methyl ester (41) may be aromatized and hydrolyzed to the acid (44) by a procedure described previously in scheme 6.

Preparing the Tetracyclic-5-oxime Compounds

The tetracyclic-5-oxime compounds of the invention can be prepared following the protocol of Scheme 7 below;

To introduce the oxime functionality, the methyl ester of the tetracyclic glyoxylamide (compound (33) in Scheme 5) is heated with hydroxylamine hydrochloride (when R is H) in a THF/methanol mixture for about 1 to 8 hours or until the reaction is deemed complete. The reaction product is isolated by chromatography or other known laboratory procedure. Substituted oximes such as when R is methyl, ethyl, phenyl or other substituent can be prepared by reacting the corresponding substituted hydroxylamine hydrochloride or free base with the glyoxylamide (33) as described supra. The ester functionality at the 6- or 7-position on the tetracyclic nucleus, as in for example, compound (45) can be: (a) converted to the acid by hydrolysis using lithium hydroxide or other known ester hydrolysis methods to afford compounds (49); or (b) isolated as the sodium salt (47) or potassium or other metal salt depending on the base used; or (c) aromatized to the naphthyl compound (47) by using DDQ under reaction conditions similar to that described in the example. The compound of formula (47) may than be hydrolyzed to the free acid compound (48). Compound (45) could be aromatized and then hydrolyzed to afford compound (48) directly.

The Acylamino Acid Compounds

The acylamino derivative of compounds 9, 19, 20, 23, 25, 35, 36, 43, 44, 48 or 49 representing compounds described above as per schemes 1 through scheme 7. Any of the compounds 9, 19, 20, 23, 25, 35, 36, 43, 44, 48 or 49 each having a oxyacetic acid group at the 6 position may be converted to the corresponding acylamino acid compound by reaction with a C-terminal protected amino acid. Where a C-terminal protected amino acid is used the protected

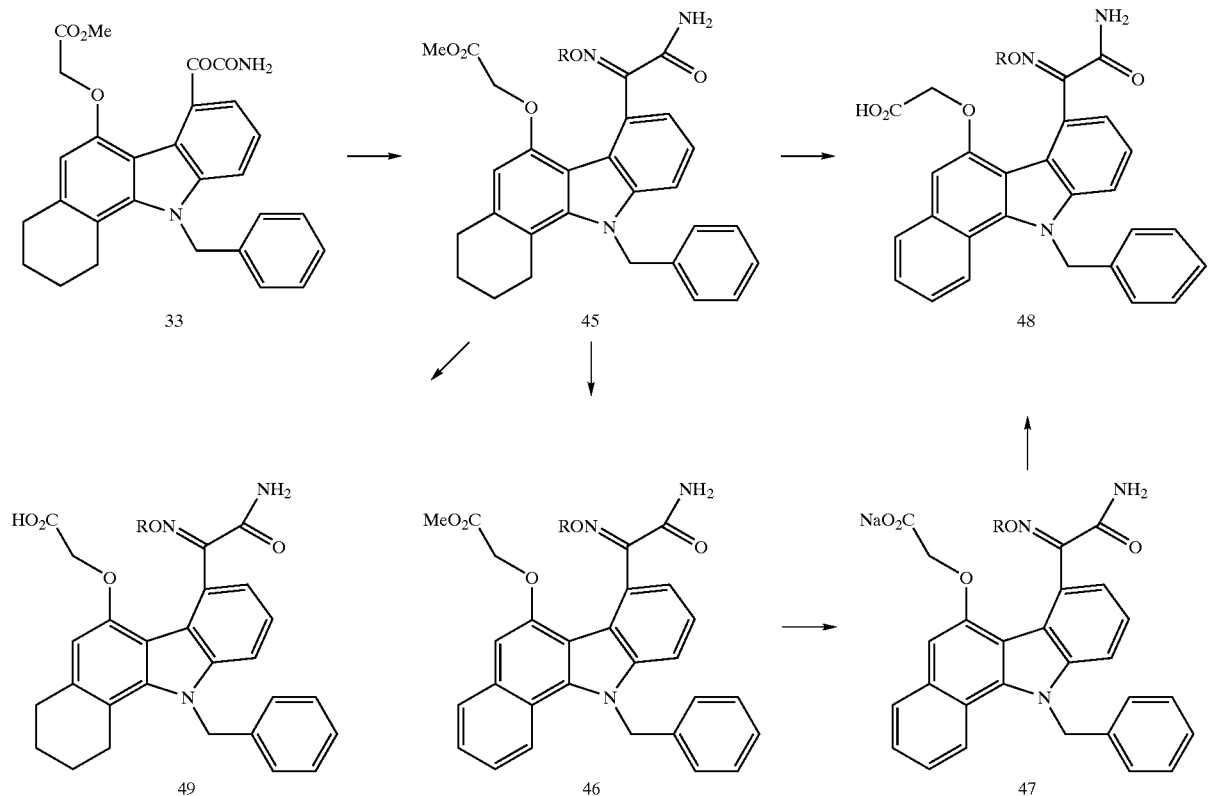

Scheme 7 amide compound or the resulting oxo-amino acid compound (e.g. compound 50 infra) is also a compound of the present invention. For example, the tetracyclic-5-glyoxylamide-6-acylamino acid derivative compounds of the invention are prepared by room temperature base catalyzed condensation of the amino acid protected at the C-terminus by a protecting group (known in the literature and preferably protected as the methyl ester), with the tetracyclic-5-glyoxylamide acid derivative compound of formula (35) as shown in Scheme 8 below:

Scheme 8

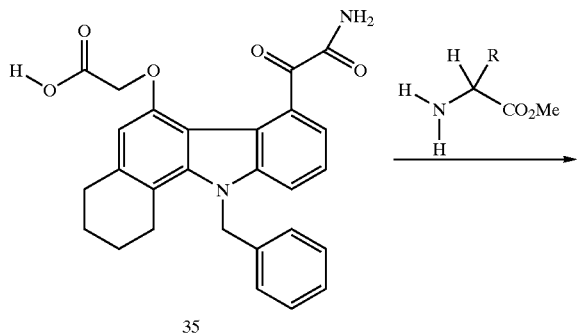

35

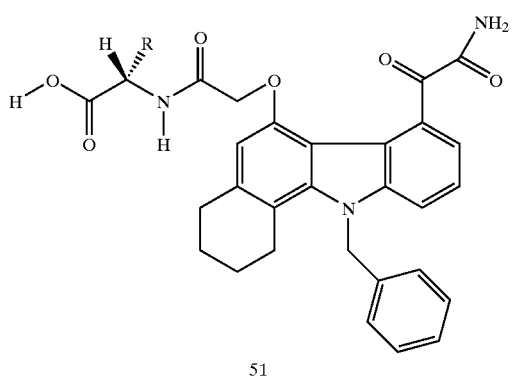

50

↓

51

The product of the condensation reaction (50), itself a compound of the invention, is hydrolyzed to the free acid to remove the amino acid protecting group. Typically, the condensation or coupling is performed in a solvent such as dimethylformamide, tetrahydrofuran or aqueous mixtures of the like. In general protic solvents are preferred for the purpose of this invention. The reaction is base catalyzed, including use of weak organic or inorganic bases. Organic bases such as collidine are preferred. The reaction is also preferably run in the presence of agents that retard or reduce racemization of the amino acid or its derivative, such as for example, benzotriazolyl-N-oxy-tris(dimethylamino) phosphonium hexafluorophosphate. Upon completion of the reaction, the mixture is concentrated in vacuo. The resulting product mixture is chromatographed or subjected to crystallization conditions to obtain the target compound (i.e. compound (51)).

Other suitable amino acid forming reactions and methods are applicable to introduce the acylamino acid functionality and are well known in the art. References texts include for example J. March *Advanced Organic Chemistry*, $3^{rd}$ ed., 1985, Wiley Interscience publishers, New York, N.Y., and R. C. Larock *Comprehensive Organic Transformations*, VCH Publishers, New York, N.Y., 1989.

Acylamino acid derivatives of the tetracyclic oximes, oxime amide, thioacetamides and acetamides may be prepared from the corresponding acid such as compound (48) (scheme 7) by methods described above for preparing the acylamino acid derivatives of the glyoxylamide compounds. For example the oxime amide compound (48) (scheme 7), above may be converted to the corresponding acylamino acid derivative by an amide coupling reaction. Similarly, the tetracyclic-5-acetamide oxyacid compounds (i.e. compound (43)), may be converted to the corresponding acylamino acid derivative at the 6- or 7-position as described previously.

Preparing the Tetracyclic-6-N-hydroxyfunctional Amide Compounds

The tetracyclic-5-glyoxylamide-6-N-hydroxyfunctional amide compounds of the invention may be prepared from the compounds 9, 19, 20, 23, 25, 35, 36, 43, 44, 48 or 49 representing the teracyclic-5-amide, the tetracyclic-5-hydrazide, the tetracyclic-5-glyoxylamide, the tracyclic-5-acetamide and the tetracyclic-5-oxime compounds prepared as described previously. Any of the compounds 9, 19, 25, 31, 38a or 40 each having a oxyacid group at the 6 position may be converted to the corresponding N-hydroxyfunctional amide compounds of the present invention by methods known to one of skill in the art. In the protocol beginning with acid compound (9), the acid (9) is converted to the N-hydroxyfunctional amide compound (52) or (53) as shown in Scheme 9 below:

Scheme 9

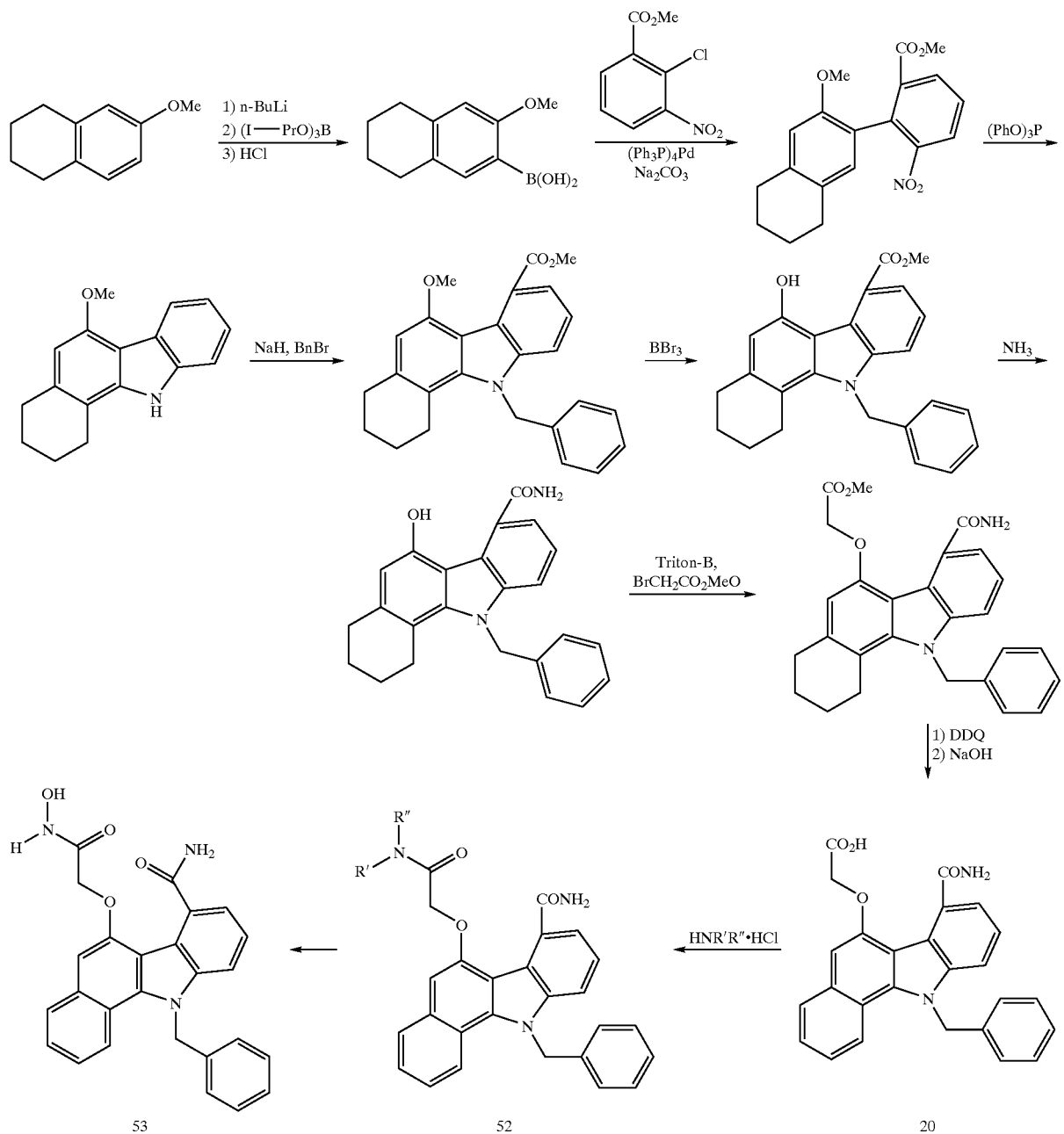

The above transformation may be accomplished by coupling the compound of formula (20), prepared as described in Scheme 3, with a protected and substituted or unsubstituted hydroxylamine group or derivative, in the presence of a coupling agent. This results in a protected N-hydroxyfunctional amide derivative compound (52). In a specific example, the acid compound (20) is reacted with o-(tert-butyldimethylsilyl) hydroxylamine ( i.e. R' is tert-butyldimethylsilyl, R" is OH) at ambient temperature in the presence of excess 2,4,6-collidine (collidine) and benzotriazol-1-yl-oxytris(dimethylamino)phosphonium hexafluorophosphonate (coupling catalyst, see *Tetrahedron Lett.*, 1219 (1975)) to afford after about 1–10 hours, the o-(tert-butyldimethylsilyl) substituted N-hydroxyfunctional amide derivative (i.e. 52). The silyl or other protecting group is removed by well known methods such as for example, the use of trifluoroacetic acid (for silyl protecting groups) to afford the desired N-hydroxyfunctional amide compound (53) wherein the hydroxy group corresponds to $R^{6a}$ and the hydrogen atom corresponds to $R^{6b}$.

Typically, the condensation or coupling tetracyclic oxyacetic compound of the invention, e.g. compound (20), to hydroxylamine or a protected derivative thereof, is performed in a solvent such a dimethylformamide, tetrahydrofuran or aqueous mixtures of the like. In general, protic solvents are preferred for the purpose of this invention. A base including for example, weak organic or inorganic bases catalyzes the reaction. Organic bases such as collidine are preferred. The reaction is also preferably run in the presence of agents that retard or reduce racemization of the hydroxy-functional amide, the substituted hydroxylamine, or its derivative. A particularly preferred agent is benzotriazolyl-N-oxy-tris(dimethylamino)phosphonium hexafluorophosphate. Upon completion of the reaction, the mixture is concentrated in vacuo. The resulting product mixture is chromatographed or crystallized, e.g., by sonication to obtain the target compound.

An alternate preparation method is the inter-conversion of compounds of the invention as shown for example in Scheme 10:

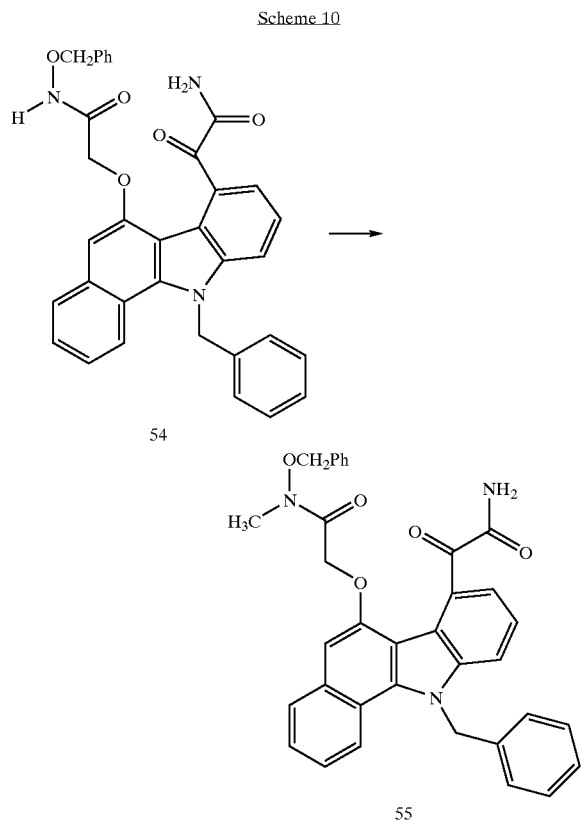

The compound of formula (54) can be converted to the compound of formula (55) by the use of a base, e.g., n-butyllithium, and an electrophile, e.g., methyl iodide. These and other methods of functional group interconversion are well known in the arts and can be found in reference texts such as for example J. March *Advanced Organic Chemistry*, Wiley Interscience publishers, New York, N.Y., 1985, and R. C. Larock *Comprehensive Organic Transformations*, VCH Publishers, New York, N.Y., 1989.

Other tetracyclic-6-hydroxyfunctional sPLA$_2$ derivative compounds disclosed herein, including for example, the tetracyclic-5-acetamide-6-hydroxyfunctional amide derivative sPLA$_2$ inhibitors are similarly prepared by condensation of the protected or unprotected, substituted or unsubstituted hydroxylamine or derivative thereof, as discussed above.

IV. Methods of Using the Compounds of the Invention

The tetracyclic compounds described herein are believed to achieve their beneficial therapeutic action principally by direct inhibition of mammalian (including human) sPLA$_2$, and not by acting as antagonists for arachidonic acid, nor other active agents below arachidonic acid in the arachidonic acid cascade, such as 5-lipoxygenases, cyclooxygenases, etc.

The method of the invention for inhibiting sPLA$_2$ mediated release of fatty acids comprises contacting mammalian sPLA$_2$ with a therapeutically effective amount of tetracyclic compounds corresponding to Formulae (I) or (II) or (III) or (IV) or (V) or (VI) or (VII) or (VIII) as described herein including a combination thereof, salt or a prodrug derivative thereof.

Another aspect of this invention is a method for treating Inflammatory Diseases such as inflammatory bowel disease, septic shock, adult respiratory distress syndrome, pancreatitis, trauma, asthma, bronchial asthma, allergic rhinitis, rheumatoid arthritis, osteoarthritis, and related diseases which comprises administering to a mammal (including a human) a therapeutically effective dose of the tetracyclic compound of the invention (see, formulae I).

As previously noted the compounds of this invention are useful for inhibiting sPLA$_2$ mediated release of fatty acids such as arachidonic acid. By the term, "inhibiting" is meant the prevention or therapeutically significant reduction in release of sPLA$_2$ initiated fatty acids by the compounds of the invention. By "pharmaceutically acceptable" it is meant the carrier, diluent or excipient must be compatible with the other ingredients of the formulation and not deleterious to the recipient thereof.

The specific dose of a compound administered according to this invention to obtain therapeutic or prophylactic effects will, of course, be determined by the particular circumstances surrounding the case, including, for example, the compound administered, the route of administration and the condition being treated. Typical daily doses will contain a non-toxic dosage level of from about 0.01 mg/kg to about 50 mg/kg of body weight of an active compound of this invention.

Preferably compounds of the invention (per Formula (I) or (II) or (III) or (IV) or (V) or (VI) or (VII) or (VIII)) or pharmaceutical formulations containing these compounds are in unit dosage form for administration to a mammal. The unit dosage form can be a capsule or tablet itself, or the appropriate number of any of these. The quantity of Active ingredient in a unit dose of composition may be varied or adjusted from about 0.1 to about 1000 milligrams or more according to the particular treatment involved. It may be appreciated that it may be necessary to make routine variations to the dosage depending on the age and condition of the patient. The dosage will also depend on the route of administration.

The compound can be administered by a variety of routes including oral, aerosol, rectal, transdermal, subcutaneous, intravenous, intramuscular, and intranasal.

Pharmaceutical formulations of the invention are prepared by combining (e.g., mixing) a therapeutically effective amount of the tetracyclic compound of the invention together with a pharmaceutically acceptable carrier or diluent therefor. The present pharmaceutical formulations are prepared by known procedures using well-known and readily available ingredients.

In making the compositions of the present invention, the Active ingredient will usually be admixed with a carrier, or diluted by a carrier, or enclosed within a carrier which may be in the form of a capsule, sachet, paper or other container. When the carrier serves as a diluent, it may be a solid., semi-solid or liquid material which acts as a vehicle, or can be in the form of tablets, pills, powders, lozenges, elixirs, suspensions, emulsions, solutions, syrups, aerosols (as a solid or in a liquid medium), or ointment, containing, for example, up to 10% by weight of the active compound. The compounds of the present invention are preferably formulated prior to administration.

For the pharmaceutical formulations any suitable carrier known in the art can be used. In such a formulation, the carrier may be a solid, liquid, or mixture of a solid and a liquid. For example, for intravenous injection the compounds of the invention may be dissolved in at a concentration of 2 mg/ml in a 4% dextrose/0.5% Na citrate aqueous solution. Solid form formulations include powders, tablets and capsules. A solid carrier can be one or more substance, which may also act as flavoring agents, lubricants, solubilizers, suspending agents, binders, tablet disintegrating agents and encapsulating material.

Tablets for oral administration may contain suitable excipients such as calcium carbonate, sodium carbonate, lactose, calcium phosphate, together with disintegrating agents, such as maize, starch, or alginic acid, and/or binding agents, for example, gelatin or acacia, and lubricating agents such as magnesium stearate, stearic acid, or talc.

In powders the carrier is a finely divided solid which is in admixture with the finely divided Active ingredient. In tablets the Active ingredient is mixed with a carrier having the necessary binding properties in suitable proportions and compacted in the shape and size desired. The powders and tablets preferably contain from about 1 to about 99 weight percent of the Active ingredient which is the novel compound of this invention. Suitable solid carriers are magnesium carbonate, magnesium stearate, talc, sugar lactose, pectin, dextrin, starch, gelatin, tragacanth, methyl cellulose, sodium carboxymethyl cellulose, low melting waxes, and cocoa butter.

Sterile liquid form formulations include suspensions, emulsions, syrups and elixirs.

The Active ingredient can be dissolved or suspended in a pharmaceutically acceptable carrier, such as sterile water, sterile organic solvent or a mixture of both. The Active ingredient can often be dissolved in a suitable organic solvent, for instance aqueous propylene glycol. Other compositions can be made by dispersing the finely divided Active ingredient in aqueous starch or sodium carboxymethyl cellulose solution or in a suitable oil.

The following pharmaceutical formulations 1 through 8 are illustrative only and are not intended to limit the scope of the invention in any way. "Active ingredient", refers to a compound according to Formula (I) or (II) or (II') or (II") or (III) or (IV) or (V) or (VI) or (VII) or (VIII) or a pharmaceutically acceptable salt, solvate, or prodrug thereof.

Formulation 1
Hard gelatin capsules are prepared using the following ingredients:

|  | Quantity (mg/capsule) |
|---|---|
| Active ingredient | 250 |
| Starch, dried | 200 |
| Magnesium stearate | 10 |
| Total | 460 mg |

Formulation 2
A tablet is prepared using the ingredients below:

|  | Quantity (mg/tablet) |
|---|---|
| Active ingredient | 250 |
| Cellulose, microcrystalline | 400 |
| Silicon dioxide, fumed | 10 |
| Stearic acid | 5 |
| Total | 665 mg |

The components are blended and compressed to form tablets each weighing 665 mg

Formulation 3
An aerosol solution is prepared containing the following components:

|  | Weight |
|---|---|
| Active ingredient | 0.25 |
| Ethanol | 25.75 |
| Propellant 22 (Chlorodifluoromethane) | 74.00 |
| Total | 100.00 |

The active compound is mixed with ethanol and the mixture added to a portion of the propellant 22, cooled to −30° C. and transferred to a filling device. The required amount is then fed to a stainless steel container and diluted with the remainder of the propellant. The valve units are then fitted to the container.

Formulation 4
Tablets, each containing 60 mg of Active ingredient, are made as follows:

| Active ingredient | 60 mg |
|---|---|
| Starch | 45 mg |
| Microcrystalline cellulose | 35 mg |
| Polyvinylpyrrolidone (as 10% solution in water) | 4 mg |
| Sodium carboxymethyl starch | 4.5 mg |
| Magnesium stearate | 0.5 mg |
| Talc | 1 mg |
| Total | 150 mg |

The Active ingredient, starch and cellulose are passed through a No. 45 mesh U.S. sieve and mixed thoroughly. The aqueous solution containing polyvinylpyrrolidone is mixed with the resultant powder, and the mixture then is passed through a No. 14 mesh U.S. sieve. The granules so produced are dried at 50° C. and passed through a No. 18 mesh U.S. sieve. The sodium carboxymethyl starch, magnesium stearate and talc, previously passed through a No. 60 mesh U.S. sieve, are then added to the granules which, after mixing, are compressed on a tablet machine to yield tablets each weighing 150 mg.

Formulation 5
Capsules, each containing 80 mg of Active
ingredient, are made as follows:

| Active ingredient | 80 mg |
|---|---|
| Starch | 59 mg |
| Microcrystalline cellulose | 59 mg |
| Magnesium stearate | 2 mg |
| Total | 200 mg |

The Active ingredient, cellulose, starch, and magnesium stearate are blended, passed through a No. 45 mesh U.S. sieve, and filled into hard gelatin capsules in 200 mg quantities.

Formulation 6
Suppositories, each containing 225 mg of Active
ingredient, are made as follows:

| Active ingredient | 225 mg |
|---|---|
| Saturated fatty acid glycerides | 2,000 mg |
| Total | 2,225 mg |

The Active ingredient is passed through a No. 60 mesh U.S. sieve and suspended in the saturated fatty acid glycerides previously melted using the minimum heat necessary. The mixture is then poured into a suppository mold of nominal 2 g capacity and allowed to cool.

Formulation 7

Suspensions, each containing 50 mg of Active ingredient per 5 ml dose, are made as follows:

| Active ingredient | 50 mg |
|---|---|
| Sodium carboxymethyl cellulose | 50 mg |
| Syrup | 1.25 ml |
| Benzoic acid solution | 0.10 ml |
| Flavor | q.v. |
| Color | q.v. |
| Purified water to total | 5 ml |

The Active ingredient is passed through a No. 45 mesh U.S. sieve and mixed with the sodium carboxymethyl cellulose and syrup to form a smooth paste. The benzoic acid solution, flavor and color are diluted with a portion of the water and added, with stirring. Sufficient water is then added to produce the required volume.

Formulation 8

An intravenous formulation may be prepared as follows:

| Active ingredient | 100 mg |
|---|---|
| Isotonic saline | 1,000 ml |

The solution of the above ingredients generally is administered intravenously to a subject at a rate of 1 ml per minute.

Assay

The following chromogenic assay procedure was used to identify and evaluate inhibitors of recombinant human secreted phospholipase $A_2$. The assay described herein has been adapted for high volume screening using 96 well microtiter plates. A general description of this assay method is found in the article, "Analysis of Human Synovial Fluid Phospholipase $A_2$ on Short Chain Phosphatidylcholine-Mixed Micelles: Development of a Spectrophotometric Assay Suitable for a Microtiterplate Reader", by Laure J. Reynolds, Lori L. Hughes, and Edward A Dennis, *Analytical Biochemistry*, 204, pp. 190–197, 1992 (the disclosure of which is incorporated herein by reference):

Reagents:

| REACTION BUFFER | |
|---|---|
| $CaCl_2.2H_2O$ | (1.47 g/L) |
| KCl | (7.455 g/L) |
| Bovine Serum Albumin (fatty acid free) (Sigma A-7030, product of Sigma Chemical Co., St. Louis MO, USA) | (1 g/L) |
| TRIS HCl | (3.94 g/L) |
| pH 7.5 (adjust with NaOH) | |
| ENZYME BUFFER | |
| 0.05 $NaOAc.3H_2O$, pH 4.5 | |
| 0.2 NaCl | |
| Adjust pH to 4.5 with acetic acid | |
| DTNB - 5,5'-dithiobis-2-nitrobenzoic acid | |
| RACEMIC DIHEPTANOYL THIO - PC | |
| racemic 1,2-bis(heptanoylthio)-1,2-dideoxy-sn-glycero-3-phosphorylcholine | |
| TRITON X-100 ™ prepare at 6.249 mg/ml in reaction buffer to equal 10 uM. | |

Reaction Mixture

A measured volume of racemic diheptanoyl thio PC supplied in chloroform at a concentration of 100 mg/ml is taken to dryness and redissolved in 10 millimolar TRITON X-100™ nonionic detergent aqueous solution. Reaction Buffer is added to the solution, then DTNB to give the Reaction Mixture.

The reaction mixture thus obtained contains 1 mM diheptanoly thio-PC substrate, 0.29 mm Triton X-100™ detergent, and 0.12 mm DTMB in a buffered aqueous solution at pH 7.5.

Assay Procedure:
1. Add 0.2 ml reaction mixture to all wells;
2. Add 10 ul test compound (or solvent blank) to appropriate wells, mix 20 seconds;
3. Add 50 nanograms of $sPLA_2$ (10 microliters) to appropriate wells;
4. Incubate plate at 40° C. for 30 minutes;
5. Read absorbance of wells at 405 nanometers with an automatic plate reader.

Tests were done in triplicate. Typically, compounds were tested at a final concentration of 5 ug/ml. Compounds were considered active when they exhibited 40% inhibition or greater compared to uninhibited control reactions when measured at 405 nanometers. Lack of color development at 405 nanometers evidenced inhibition. Compounds initially found to be active were re-assayed to confirm their activity and, if sufficiently active, $IC_{50}$ values were determined. Typically, the $IC_{50}$ values (see, Table I, below) were determined by diluting test compound serially two-fold such that the final concentration in the reaction ranged from 45 ug/mL to 0.35 ug/ml. More potent inhibitors required significantly greater dilution. In all cases, % inhibition measured at 405 nanometers generated by enzyme reactions containing inhibitors relative to the uninhibited control reactions was determined. Each sample was titrated in triplicate and result values were averaged for plotting and calculation of $IC_{50}$ values. $IC_{50}$ values were determined by plotting log concentration versus inhibition values in the range from 10–90% inhibition.

| Results | |
|---|---|
| Compound of Example # | $IC_{50}$ (uM) (micromolar) |
| 1 | 0.015 |
| 2 | 0.012 |
| 3 | 0.0094 |

While the present invention has been illustrated above by certain specific embodiments, it is not intended that these specific examples should limit the scope of the invention as described in the appended claims.

EXPERIMENTAL

All of the products of the Examples described below as well as intermediates used in the following procedures showed satisfactory NMR and IR spectra. They also had the correct mass spectral values.

Example 1

Part A.

6-Methoxy-5,6,7,8-tetrahydronaphthalene-7-boronic acid

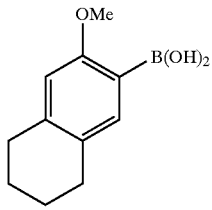

A −78° C. solution of 10.0 g (61.6 mmol) of 6-methoxy-5,6,7,8-tetrahydronaphthalene in 75 mL of THF was treated in a dropwise manner with 42.0 mL (67.2 mmol) of 1.6 M n-BuLi in hexanes. The mixture was stirred for 1 hr and was treated with 14.8 mL (64.1 mmol) of triisopropyl borate. The reaction was allowed to warm slowly to 0° C. and was stirred at this temperature for 0.5 hr. The reaction was quenched by the careful addition of 120 mL of aq 1N HCl. The layers were separated and the aqueous layer extracted with EtOAc (3×50 mL). The combined organic layers were dried over $Na_2SO_4$, filtered, and concentrated in vacuo to afford a white solid which was used in part B without further purification.

Part B.

2-(6-Methoxy-5,6,7,8-tetrahydronaphthalen-2-yl)-3-nitrobenzoic Acid Methyl Ester

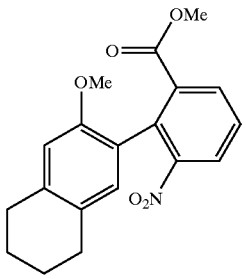

A solution of 5.69 g (26.5 mmol) of methyl 2-chloro-3-nitrobenzoate and 6.00 g (29.1 mmol) of the boronic acid from Part A in 110 mL of THF was treated with 1.68 g of tetrakis(triphenylphosphine)palladium(0) followed by 29.1 mL (58.2 mmol) of 2.0 N $Na_2CO_3$. The mixture was flushed with a stream of $N_2$ and heated to mild reflux for 48 hrs. The reaction was allowed to cool and was extracted with EtOAc (5×100 mL). The combined organic layers were washed sequentially with $H_2O$, 1 N aq HCl, saturated aq $NaHCO_3$, and $H_2O$. The organic layers were dried over $Na_2SO_4$, filtered and concentrated in vacuo 12.4 g of crude material. The residue was purified by flash chromatography ($SiO_2$; 30% hexanes in toluene to 100% toluene) to afford 3.88 g (43%) of the title compound. $^1H$ NMR (DMSO-$d_6$) δ 8.04 (dd, J=8.1 and 1.1 Hz, 1H), 7.94 (dd, J=7.7 and 1.1 Hz, 1H), 7.68–7.61 (m, 1H), 6.69–6.64 (m, 2H), 3.54 (m, 6H), 2.74–2.67 (m, 2H), 2.61–2.53 (m, 2H), 1.74–1.64 (m, 4H); IR ($CHCl_3$) 2936, 1735, 1535, 1511, 1465, 1298, 1268, 1126 $cm^{-1}$; FDMS 342 (M+1).

Part C.

6-Methoxy-2,3,4,11-tetraydro-1H-benzo[a]carbazole-7-carboxylic Acid Methyl Ester

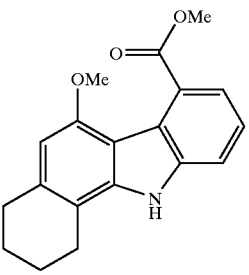

A 3.75 g (11.0 mmol) sample of the product from Part B was taken up in triphenylphospite in a sealed tube and the mixture heated to 160° C. for 23 hrs. The reaction was allowed to cool and was placed on a column of $SiO_2$. Elution with 5% EtOAc in hexanes then 15% EtOAc in hexanes provided 2.10 g (63%) of the title compound as well as 587 mg of starting material. $^1H$ NMR (DMSO-$d_6$) δ 11.26 (s, 1H), 7.52 (d, 7.7 Hz, 1H), 7.32–7.26 (m, 1H), 7.04 (d, J=7.3 Hz, 1H), 6.36 (s, 1H), 3.82 (s, 3H), 3.81 (s, 3H), 2.85–2.76 (m, 4H), 1.89–1.77 (m, 4H); IR ($CHCl_3$) 3472, 2938, 1725, 1619, 1609, 1520, 1297, 1148, 1020 $cm^{-1}$; FDMS 310 (M+1).

Part D.

11-Benzyl-6-methoxy-2,3,4,11-tetraydro-1H-benzo[a]carbazole-7-carboxylic Acid Methyl Ester

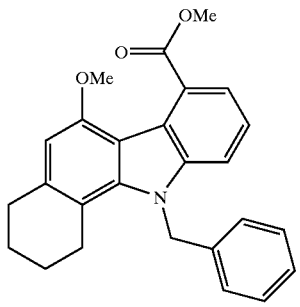

A solution of 2.00 g (6.47 mmol) of the product from Part C in 40 mL of DMF was cooled to 0° C. and treated with 0.23 g (9.70 mmol; 60% in mineral oil) of NaH. The mixture was stirred for 0.5 hr and treated with 1.15 mL (9.70 mmol) of benzyl bromide. The reaction was allowed to warm to ambient temperature, stirred for overnight, and quenched by the careful addition of H$_2$O (50 mL). The mixture was extracted with EtOAc (4×100 mL). The combined organic layers were washed with H$_2$O (3×100 mL), dried, filtered, and concentrated in vacuo to afford 2.93 g of an off-white solid. The residue was purified by flash chromatography (50% CHCl$_3$ in hexanes then 100% CHCl$_3$) to afford 2.38 g (92%) of the title compound. $^1$H NMR (DMSO-d$_6$) δ 7.50 (d, 7.7 Hz, 1H), 7.32–7.26 (m, 1H), 7.26–7.21 (m, 2H), 7.19–7.12 (m, 1H), 7.10 (dd, J=7.3 and 1.0 Hz, 1H), 6.86 (d, J=7.0 Hz, 2H), 6.45 (s, 1H), 3.83 (s, 3H), 3.82 (s, 3H), 3.04–2.97 (m, 2H), 2.87–2.81 (m, 2H), 1.69–1.63 (m, 4H); IR (CHCl$_3$) 2937, 1725, 1584, 1433, 1335, 1323, 1290, 1168, 1144 cm$^{-1}$; FDMS 400 (M+1).

Part E.

11-Benzyl-6-hydroxy-2,3,4,11-tetraydro-1H-benzo[a]carbazole-7-carboxylic Acid Methyl Ester

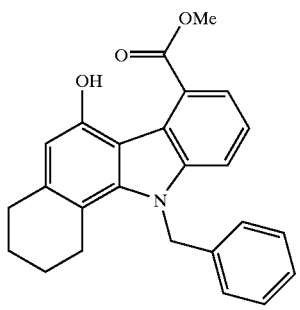

A solution of 1.50 g (3.76 mmol) of the product from Part D in 45 mL of CH$_2$Cl$_2$ was cooled to −10° C. and treated with 0.50 mL (5.26 mmol) of BBr$_3$. The reaction was stirred at −10° C. for 1 hr, 30 mL MeOH was carefully added, and the mixture stirred for 10 min. The mixture was transferred to a separatory funnel and saturated aqueous NaHCO$_3$ (10 mL) was added. The mixture was extracted with EtOAc (3×50 mL) and the combined organic layers dried over Na$_2$SO$_4$, filtered, and concentrated in vacuo to afford 1.38 g of the title compound. The product was taken on without further purification. $^1$H NMR (DMSO-d$_6$) δ 9.82 (s, 1H), 7.44 (dd, 7.7 and 1.0 Hz, 1H), 7.20–7.15 (m, 4H), 7.07 (dd, J=7.3 and 1.1 Hz, 1H), 6.88 (d, J=7.0 Hz, 1H), 6.29 (s, 1H), 5.82 (s, 2H), 3.77 (s, 3H), 3.34–3.28 (m, 2H), 3.00–2.93 (m, 2H), 2.77–2.71 (m, 2H), 1.66–1.58 (m, 4H); FDMS 386 (M+1).

Part F.

11-Benzyl-6-hydroxy-2,3,4,11-tetraydro-1H-benzo[a]carbazole-7-carboxylic Acid Amide

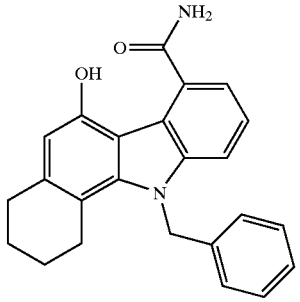

A solution of 1.37 g (3.58 mmol) of the product from Part E in 15 mL of THF was cooled to −78° C. and the solution treated with a stream of ammonia gas. After ~10 mL of ammonia condensed, the vessel was sealed and the reaction stirred at ambient temperature for 66 hrs and at 50° C. for 24 hrs. The volatiles were allowed to evaporate and the residue triturated with EtOAc then hexanes to afford 910 mg (69%) of the title compound. $^1$H NMR (DMSO-d$_6$) δ 9.85 (br s, 1H), 8.61 (br s, 1H), 8.16 (br s, 1H), 7.54–7.48 (m, 1H), 7.34–7.29 (m, 2H), 7.27–7.14 (m, 3H), 6.88 (d, 7.3 Hz, 2H), 6.34 (s, 1H), 5.86 (s, 2H), 3.06–2.97 (m, 2H), 2.80–2.73 (m, 2H), 1.68–1.59 (m, 4H); IR (KBr) 3329, 3197, 2922, 1690, 1604, 1584, 1494, 1440, 1333, 1298, 698 cm$^{-1}$; FDMS 371 (M+1).

Part G.

(11-Benzyl-7-carbamoyl-2,3,4,11-tetraydro-1H-benzo[a]carbazol-6-yloxy)acetic Acid Methyl Ester

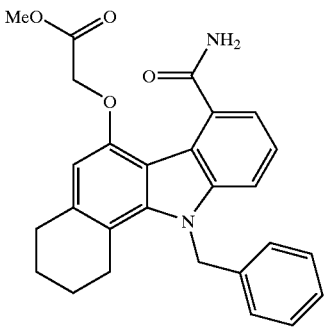

A solution of 500 mg (1.35 mmol) of the product from Part F in 10 mL DMF was treated with 880 mg of Cs$_2$CO$_3$ and the mixture stirred for 0.5 hr. Methyl bromoacetate (0.20 mL; 2.00 mmol) was added dropwise and the reaction stirred at ambient temperature for 18 hr. The reaction was quenched by the addition of 20 mL H$_2$O and the mixture extracted with EtOAc (4×50 mL). The combined organic layers were dried over Na$_2$SO$_4$, filtered, and concentrated in vacuo to afford 700 mg of a brown solid. Purification by radial chromatography (SiO$_2$; 80% EtOAc in hexanes) afforded 504 mg of the title compound. $^1$H NMR (DMSO-d$_6$) δ 7.46 (br s, 1H), 7.38 (d, 8.4 Hz, 1H), 7.29–7.16 (m, 4H), 7.10 (br s, 1H), 6.88 (d, 7.3 H, 2H), 6.28 (s, 1H), 5.87 (s, 2H), 4.82 (s, 2H), 3.69 (s, 3H), 3.04–2.98 (m, 2H), 2.81–2.74 (m, 2H), 1.69–1.59 (m, 4H); FDMS 443 (M+1).

Part H.

(11-Benzyl-7-carbamoyl-2,3,4,11-tetraydro-1H-benzo[a]carbazol-6-yloxy)acetic Acid

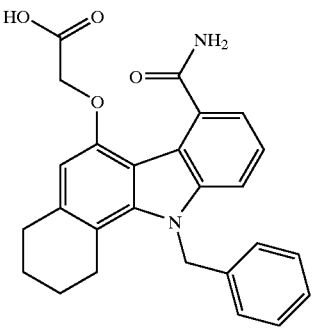

A solution of 50 mg (0.11 mmol) of the product from Part G in 0.12 mL MeOH and 0.37 mL THF was treated with 0.12 mL of 1 N aq NaOH (0.12 mmol). The mixture was stirred for 6 hrs, diluted with 0.5 mL of THF, filtered and the solid dried to afford 49 mg of the title compound. $^1$H NMR (DMSO-$d_6$) δ 7.61 (br s, 1H), 7.36 (d, 8.4 Hz, 1H), 7.27–7.15 (m, 5H), 7.01 (d, J=7.3 Hz, 1H), 6.88 (d, 7.3 Hz, 2H), 6.21 (s, 1H), 5.83 (s, 2H), 4.21 (s, 2H), 3.03–2.97 (m, 2H), 2.79–2.71 (m, 2H), 1.70–1.58 (m, 4H); IR (KBr) 3462, 1661, 1615, 1590, 1438, 1411, 1330, 1176 cm−1; FDMS 427 (M−1).

Example 2

Part A.

6-Methoxyindane-5-boronic acid

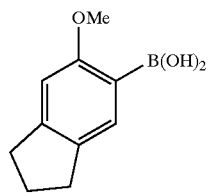

A solution of 1.06 g (4.69 mmol) of 5-bromo-6-methoxyindane in 10 mL of THF was cooled to −78° C. and treated in a dropwise manner with 2.90 mL (4.64 mmol) of 1.6 M n-BuLi in hexanes. The mixture was stirred for 1 hr and was treated with 1.90 mL (8.2 mmol) of triisopropyl borate. The reaction was allowed to warm slowly to 0° C. and was stirred at this temperature for 0.5 hr. The reaction was quenched by the careful addition of 12 mL of aq 1N HCl. The layers were separated and the aqueous layer extracted with EtOAc (3×50 mL). The combined organic layers were dried over $Na_2SO_4$, filtered, and concentrated in vacuo to afford 1.02 g. Flash chromatography ($SiO_2$; 15% EtOAc in hexanes) gave 0.62 g (69%) of the title compound as a white solid. $^1$H NMR (DMSO-$d_6$) δ 7.52 (s, 2H), 7.41 (s, 1H), 6.84 (s, 1H), 3.75 (s, 3H), 2.81 (t, J=7.3 Hz, 2H), 2.73 (t, J=7.3 Hz, 2H), 2.00–1.92 (m, 2H); IR ($CHCl_3$) 3505 (br), 2945, 1612, 1570, 1487, 1465, 1417, 1297, 1252, 1161, 1129 cm$^{-1}$; FDMS 192 (M+).

Part B.

2-(6-Methoxyindan-5-yl)-3-nitrobenzoic acid methyl ester

A solution of 4.93 g (22.9 mmol) of methyl 2-chloro-3-nitrobenzoate and 4.00 g (20.8 mmol) of the boronic acid from Part A in 100 mL of THF was treated with 1.20 g (1.04 mmol) of tetrakis(triphenylphosphine)palladium (0) followed by 21.8 mL (43.7 mmol) of 2.0 N $Na_2CO_3$. The mixture was flushed with a stream of $N_2$ and heated to mild reflux for 26 hrs. The reaction was allowed to cool and was extracted with EtOAc (5×100 mL). The combined organic layers were washed sequentially with $H_2O$, 1 N aq HCl, $H_2O$, saturated aq $NaHCO_3$, brine and $H_2O$. The organic layers were dried over $Na_2SO_4$, filtered and concentrated in vacuo to afford 10.30 g of a yellow oil. The oil was taken up in EtOAc and was washed with 1 N aq NaOH to removed residual starting boronic acid. The resulting oil was purified by flash chromatography ($SiO_2$; 50% hexanes in toluene to 100% toluene) to afford 2.35 g of the title compound. $^1$H NMR (DMSO-$d_6$) δ 7.96 (dd, J=7.7 and 1.1 Hz, 1H), 7.90 (dd, J=8.1 and 1.1 Hz, 1H), 7.53–7.47 (m, 1H), 6.89 (s, 1H), 6.81 (s, 1H), 3.67 (s, 3H), 3.62 (s, 3H), 2.93 (t, J=7.7 Hz, 2H), 2.84 (t, J=6.3 Hz, 2H), 2.12–2.03 (m, 2H); IR ($CHCl_3$) 1736, 1535, 1466, 1297, 1269, 1129 cm$^{-1}$; FDMS 328 (M+1)

Part C.

5-Methoxy-1,2,3,10-tetraydrocyclopenta[a]carbazole-6-carboxylic Acid Methyl Ester A 2.05 g (6.27 mmol) sample of the product from Part B was taken up in 6.56 mL of triphenylphospite in a sealed tube and the mixture heated to 160° C. for 36 hrs. The reaction was cooled, an additional 8.20 mL of triphenylphophite added, and the reaction heated to 160° C. for an additional 64 hrs. The reaction was allowed to cool and was placed on a column of $SiO_2$. Elution with 5% EtOAc in hexanes then 25% EtOAc in hexanes provided 1.43 g (77%) of the title compound. $^1$H NMR (DMSO-$d_6$) δ 11.4 (s, 1H), 7.51 (dd, J=8.1 and 1.1 Hz, 1H), 7.33–7.27 (m, 1H), 7.05 (dd, J=7.3 and 0.8 Hz, 1H), 6.58 (s, 1H), 3.83 (s, 3H), 3.82 (s, 3H), 3.3.01–2.94 (m, 2H), 2.19–2.10 (m, 2H); IR (CHCl₃) 3470, 2953, 1724, 1631, 1610, 1512, 1431, 1315, 1296, 1147, 1020 cm⁻¹; FDMS 296 (M+1).

Part D.

10-Benzyl-5-methoxy-1,2,3,10-tetraydrocyclopenta[a]carbazole-6-carboxylic Acid Methyl Ester

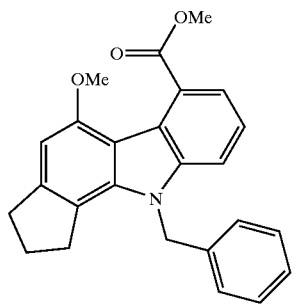

A solution of 1.28 g (4.34 mmol) of the product from Part C in 25 mL of DMF was cooled to 0° C. and treated with 0.27 g (6.51 mmol; 60% in mineral oil) of NaH. The mixture was stirred for 0.5 hr and treated with 0.77 mL (6.51 mmol) of benzyl bromide. The reaction was allowed to warm to ambient temperature, stirred for 15 hrs, and quenched by the careful addition of H₂O (100 mL). The mixture was extracted with EtOAc (3×100 mL). The combined organic layers were washed with H₂O (3×100 mL), dried over Na₂SO₄, filtered, and concentrated in vacuo. The residue was purified by flash chromatography (5% EtOAc in hexanes then 50% CHCl₃ in hexanes then 100% CHCl₃) to afford 1.37 g (83%) of the title compound. ¹H NMR (DMSO-d₆) δ 7.33 (m, 7H), 7.01–6.97 (m, 1H), 6.60 (s, 1H), 5.65 (s, 2H), 3.97 (s, 6H), 3.13 (t, J=7.3 Hz, 2H), 3.00 (t, J=7.3 Hz, 2H), 2.14–2.06 (m, 2H); FDMS 386 (M+1).

Part E.

10-Benzyl-5-hydroxy-1,2,3,10-tetraydrocyclopenta[a]carbazole-6-carboxylic Acid Methyl Ester

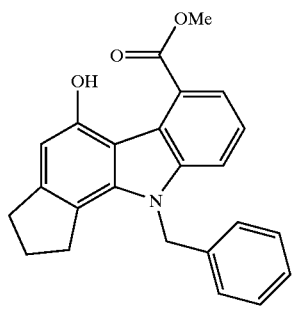

A solution of 0.46 g (1.18 mmol) of the product from Part D in 15 mL of CH₂Cl₂ was cooled to –10° C. and treated with 0.15 mL (1.54 mmol) of BBr₃. The reaction was stirred at –10° C. for 2 hrs, 5 mL MeOH was carefully added, and the mixture stirred for 1 hr. Saturated aqueous NaHCO₃ (10 mL) was added and the mixture concentrated in vacuo. The residue was extracted with EtOAc to afford a quantitative yield of the title compound. ¹H NMR (DMSO-d₆) δ 9.92 (s, 1H), 7.51 (dd, J=8.2 and 0.8 Hz, 1H), 7.31–7.17 (m, 4H), 7.07 (dd, J=7.3 and 1.1 Hz, 1H), 6.93 (d, J=7.0 Hz, 1H), 6.47 (s, 1H), 5.71 (s, 2H), 3.78 (s, 3H), 3.04 (t, J=7.3 Hz, 2H), 2.83 (t, J=7.3 Hz, 2H), 2.01–1.94 (m, 2H); IR (CHCl₃) 1684, 1497, 1442, 1287, 1269, 1150 cm⁻¹; FDMS 372 (M+1).

Part F.

10-Benzyl-5-hydroxy-1,2,3,10-tetraydrocyclopenta[a]carbazole-6-carboxylic Acid Amide

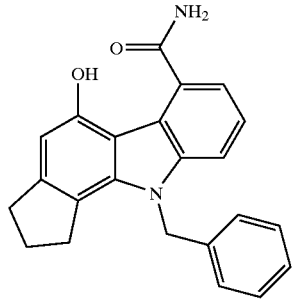

A solution of 400 mg (1.08 mmol) of the product from Part E in 10 mL of THF was cooled to –78° C. and the solution treated with a stream of ammonia gas. After ~10 mL of ammonia condensed, the vessel was sealed and the reaction stirred at ambient temperature for 4 days and at 50° C. for 2 days. The volatiles were allowed to evaporate and the residue triturated with CHCl₃ to afford 293 mg of the title compound. ¹H NMR (DMSO-d₆) δ 10.02 (s, 1H), 8.69 (br s, 1H), 8.24 (br s, 1H), 7.63–7.58 (m, 1H), 7.38–7.32 (m, 2H), 7.24–7.14 (m, 3H), 6.92–6.88 (m, 2H), 6.51 (s, 1H), 5.77 (s, 2H), 3.09 (t, J=7.3 Hz, 2H), 2.85 (t, J=7.3 Hz, 2H), 2.02–1.93 (m, 2H); IR (KBr) 3331, 3192, 1690, 1605, 1583, 1570, 1494, 1451, 1441, 1330, 1273, 799, 726, 699 cm⁻¹; FDMS 357 (M+1).

Part G.

(10-Benzyl-6-carbamoyl-1,2,3,10-tetraydrocyclopenta[a]carbazol-5-yloxy)acetic Acid Methyl Ester

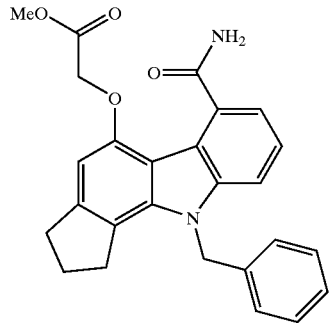

A solution of 100 mg (0.28 mmol) of the product from Part F in 3 mL DMF was cooled to 0° C. and treated with 0.17 mL of 40% aq Triton-B (0.37 mmol). The mixture was stirred at ambient temperature for 15 min and treated with 0.04 mL (0.37 mmol) of methyl bromoacetate. The reaction was stirred at ambient temperature for 2 hr and quenched by the addition of 20 mL H₂O. The mixture was extracted with EtOAc (4×30 mL) and the combined organic layers washed with H₂O (4×30 mL). The organic phase was dried over Na₂SO₄, filtered, and concentrated in vacuo to afford 147 mg of a white solid. Recrystallization from EtOAc afforded 75 mg of the title compound. ¹H NMR (DMSO-d₆) δ 7.48–7.43 (m, 2H), 7.30–7.11 (m, 5H), 7.00 (dd, J=7.3 and 0.8 Hz, 1H), 6.93 (d, J=7.3 Hz, 2H), 6.49 (s, 1H), 5.73 (s, 2H), 4.84 (s, 2H), 3.69 (s, 3H), 3.08 (t, J=7.0 Hz, 2H), 2.88 (t, J=7.3 Hz, 2H), 2.06–1.98 (m, 2H); IR (CHCl₃) 1757, 1673, 1593, 1496, 1453, 1434, 1390, 1164 cm⁻¹; FDMS 429 (M+1).
Part H.

(10-Benzyl-6-carbamoyl-1,2,3,10-tetraydrocyclopenta[a]carbazol-5-yloxy)acetic Acid

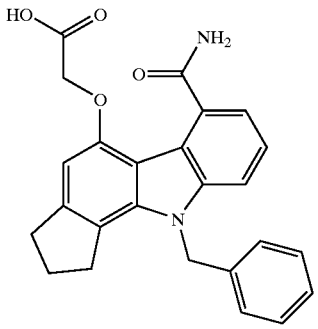

A solution of 73 mg (0.17 mmol) of the product from Part G in 0.56 mL MeOH and 0.19 mL THF was treated with 0.19 mL of 1 N aq NaOH (0.19 mmol). The mixture was stirred for 48 hrs, filtered and the solid washed with aqueous 1N HCl to afford 40 mg of pure the title compound. ¹H NMR (DMSO-d₆) δ 7.60 (br s, 1H), 7.42 (d, J=8.4 Hz, 1H), 7.34 (br s, 1H), 7.29–7.04 (m, 4H), 7.00 (d, J=7.3 Hz, 1H), 6.93 (d, J=7.3 Hz, 2H), 6.42 (s, 1H), 5.72 (s, 2H), 4.23 (s, 2H), 3.06 (t, J=7.3 Hz, 2H), 2.85 (t, J=7.3 Hz, 2H), 2.03–1.95 (m, 2H).

Example 3

(11-Benzyl-7-carbamoyl-11H-benzo[a]carbazol-6-yloxy)acetic acid methyl ester

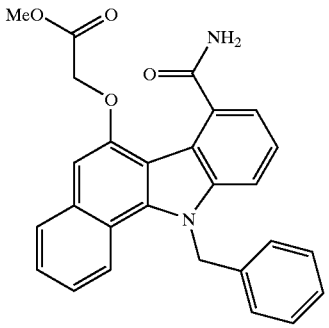

A solution of 100 mg (0.23 mmol) of (11-benzyl-7-carbamoyl-2,3,4,11-tetraydro-1H-benzo[a]carbazol-6-yloxy)acetic acid methyl ester in 3 mL of 1,4-dioxane was treated with DDQ (102 mg; 0.45 mmol) and the mixture heated to reflux for 1 hr. The reaction was allowed to cool and was diluted with 20 mL H₂O and 10 mL sat'd aq. NaHCO₃. The mixture was extracted with EtOAc (4×20 mL). The combined organic layers were washed sequentially with H₂O, sat'd aq. NaHCO₃, and H₂O, dried over Na₂SO₄, filtered and concentrated in vacuo to afford a tan solid. Purification by radial chromatography (SiO₂; 80% EtOAc in hexanes) afforded 59 mg (0.13 mmol; 59%) of the title compound. ¹H NMR (DMSO-d₆) δ 8.27 (d, J=8.8 Hz, 1H), 7.85 (d, J=8.0 Hz, 1H), 7.72 (d, J=8.1 Hz, 1H), 7.56 (br s, 1H), 7.46–7.38 (m, 2H), 7.28–7.16 (m, 6H), 7.06 (d, 7.3 Hz, 1H), 6.96 (s, 1H), 6.17 (s, 2H), 5.01 (s, 2H), 3.71 (s, 3H); FDMS 439 (M+1).

Example 4

(11-Benzyl-7-carbamoyl-11H-benzo[a]carbazol-6-yloxy)acetic acid

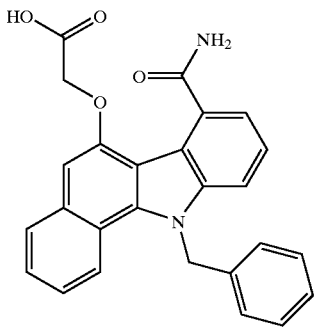

A solution of 30 mg (0.07 mmol) of the product from Part A in 0.07 mL MeOH and 0.21 mL THF was treated with 0.07 mL of 1 N aq NaOH (0.07 mmol). The mixture was stirred overnight, treated with 0.2 mL of 1N aq HCl and the resulting solid filtered and dried to afford 20 mg (0.05 mmol; 67%) of the title compound. ¹H NMR (DMSO-d₆) δ 12.89 (s, 1H), 8.27 (d, J=8.5 Hz, 1H), 7.86 (d, J=7.7 Hz, 1H), 7.79–7.72 (m, 2H), 7.49–7.38 (m, 3H), 7.30–7.17 (m, 5H), 7.05 (d, 7.2 Hz, 2H), 6.95 (s, 2H), 4.92 (s, 2H); IR (KBr) 3489, 1718, 1595, 1565, 1435, 1236, 1176, 800, 749 cm−1; FDMS 423 (M−1).

We claim:

1. A tetracyclic compound represented by the formula (I), or a pharmaceutically acceptable salt, or solvate thereof;

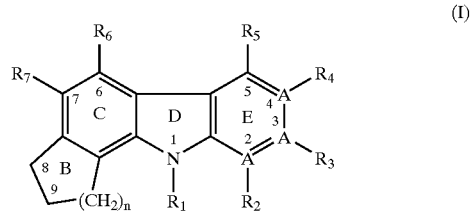

(I)

wherein
   A is C;
   n is 1, 2 or 3;
   B, C, D, and E are ring identifiers; the ring B has 0 to 3 double bonds depending on ring size;
   $R_1$ is selected from groups (a), or (b) wherein;
     (a) is $C_7$–$C_{20}$ alkyl, $C_7$–$C_{20}$ haloalkyl, $C_7$–$C_{20}$ alkenyl, or $C_7$–$C_{20}$ alkynyl;
     (b) is a member of (a) substituted with one or more substituents independently selected from the group consisting of hydrogen, $C_1$–$C_8$ alkyl, $C_2$–$C_8$ alkenyl, $C_2$–$C_8$ alkynyl, $C_7$–$C_{12}$ aralkyl, $C_7$–$C_{12}$ alkaryl, $C_3$–$C_8$ cycloalkyl, $C_3$–$C_8$ cycloalkenyl, phenyl, toluyl, xylenyl, biphenyl, $C_1$–$C_8$ alkoxy, $C_2$–$C_8$ alkenyloxy, $C_2$–$C_8$ alkynyloxy, $C_2$–$C_{12}$ alkoxyalkyl, $C_2$–$C_{12}$ alkoxyalkyloxy, $C_2$–$C_{12}$ alkylcarbonyl;
   $R_2$, $R_3$ and $R_4$ are each independently selected from the group consisting of hydrogen, $C_1$–$C_8$ alkyl, $C_2$–$C_8$ alkenyl, $C_2$–$C_8$ alkynyl, $C_7$–$C_{12}$ aralkyl, $C_7$–$C_{12}$ alkaryl, $C_3$–$C_8$ cycloalkyl, $C_3$–$C_8$ cycloalkenyl, phenyl, toluyl, xylenyl, biphenyl, $C_1$–$C_8$ alkoxy, $C_2$–$C_8$ alkenyloxy, $C_2$–$C_8$ alkynyloxy, $C_2$–$C_{12}$ alkoxyalkyl, $C_2$–$C_{12}$ alkoxyalkyloxy, $C_1$–$C_8$ haloalkyl, nitro, and cyano;

$R_5$ is -($L_5$)-Z, where -($L_5$)- is a bond, or —($CH_2$)—; and Z is selected from an amide, thioamide, oxime amide, oxime thioamide, glyoxylamide, hydrazide, or acetamide group represented by the formulae,

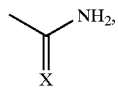

2. The compound of claim 1 wherein A is carbon and $R_2$, $R_3$, and $R_4$ are each independently hydrogen, $C_1$–$C_4$ alkyl, $C_2$–$C_4$ alkenyl, —O—($C_1$–$C_3$ alkyl), —S—($C_1$–$C_3$ alkyl), $C_3$–$C_4$ cycloalkyl, —$CF_3$, halo, —$NO_2$ or —CN.

3. The compound of claim 1 wherein for $R_5$, Z is the group represented by the formula;

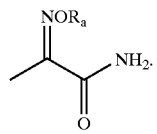

and the group -($L_5$)- is a bond; and $R_a$ is hydrogen, methyl, ethyl, propyl, isopropyl, phenyl or benzyl.

4. The compound of claim 1 wherein for $R_5$, Z is the group represented by the formula;

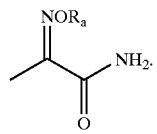

and the group -($L_5$)- is a bond; and $R_a$ is hydrogen.

5. The compound of claim 1 wherein for $R_5$, Z is the group represented by the formula;

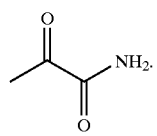

and the group -($L_5$)- is a bond.

6. The compound of claim 1 wherein for $R_5$, Z is the group represented by the formula;

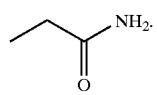

and the group -($L_5$)- is a bond.

7. The compound of claim 1 wherein for $R_5$, Z is the group represented by the formula;

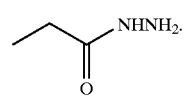

and the group -($L_5$)- is a bond.

8. The compound of claim 1 wherein for $R_5$ the group -($L_5$)- is a bond.

9. The compound of claim 1 wherein $R_6$ is the group, -($L_n$)-(N-hydroxyfunctional amide group) and wherein the (N-hydroxyfunctional amide group) is:

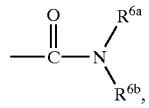

and $R^{6a}$ is independently selected from the group consisting of hydrogen, —OH, ($C_1$–$C_6$)alkoxy, and aryloxy; and wherein $R^{6b}$ is independently selected from the group consisting of H, ($C_1$–$C_6$)alkyl, arylalkyl, heteroaryl and aryl.

10. The compound of claim 1 wherein $R_6$ is the group, -($L_c$)-(acylamino acid group) and wherein the (acylamino acid group) is:

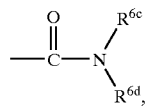

and $R^{6c}$ is selected from the group consisting of H, ($C_1$–$C_6$) alkyl, ($C_1$–$C_6$)alkoxy, heteroaryl and aryl; and wherein $NR^{6d}$ is an amino acid residue of an amino acid with the nitrogen atom being part of the amino group of the amino acid.

11. The compound of claim 1 wherein $R_6$ is the group, -L($_a$)-(acidic group) and wherein the (acidic group) is selected from the group consisting of —COOH, —COONa, and —COOK.

12. A tetracyclic compound represented by the formula (II'), or a pharmaceutically acceptable salt or solvate, thereof;

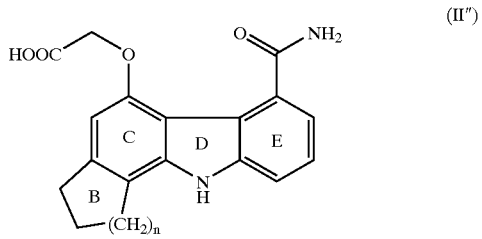

wherein;
n is 1 or 2.

13. A tetracyclic compound represented by the formula (II"), or a pharmaceutically acceptable salt or solvate thereof;

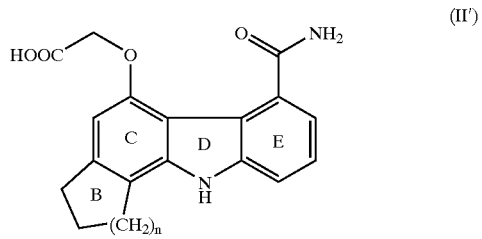

wherein;
n is 2 and B ring is fully unsaturated (i.e. B+C ring= naphthyl).

14. A compound of formula I selected from the group consisting of:

(10-Benzyl-6-carbamoyl-1,2,3,10-tetraydrocyclopenta[a]
   carbazol-5-yloxy)acetic acid methyl ester,
(10-Benzyl-6-carbamoyl-1,2,3,10-tetraydrocyclopenta[a]
   carbazol-5-yloxy)acetic acid,
(10-Benzyl-6-carbamoyl-1,2,3,10-tetraydrocyclopenta[a]
   carbazol-5-yloxy)acetic acid methyl ester,
10-Benzyl-6-carbamoyl-1,2,3,10-tetraydrocyclopenta[a]
   carbazol-5-yloxy)acetic acid,
(11-Benzyl-7-carbamoyl-2,3,4,11-tetraydro-1H-benzo[a]
   carbazol-6-yloxy)acetic acid methyl ester, and
(11-Benzyl-7-carbamoyl-2,3,4,11-tetraydro-1H-benzo[a]
   carbazol-6-yloxy)acetic acid, or a pharmaceutically
   acceptable salt or solvate thereof.

15. A tetracyclic compound represented by the formulae (C1), or (C2), or (C3) or (C4) or (C5) or (C6) or (C7) or (C8) or (C9);

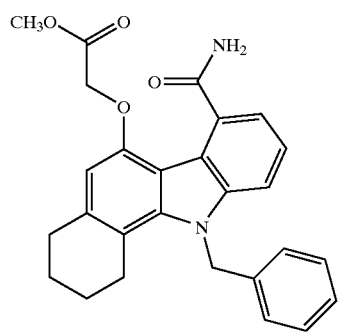
(C1)

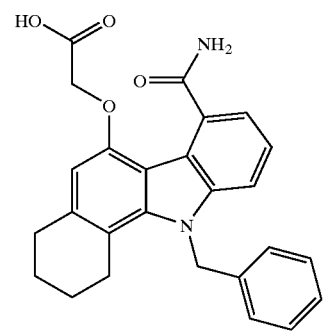
(C2)

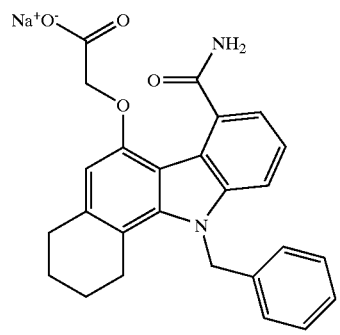
(C3)

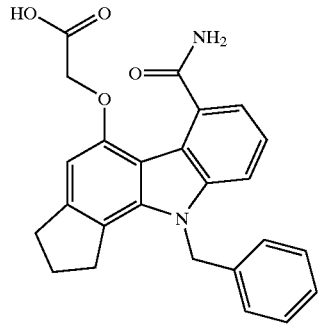
(C4)

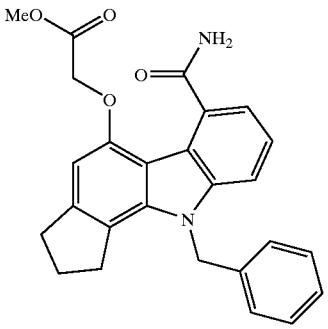
(C5)

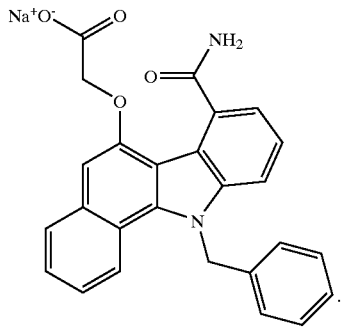
(C9)

16. A pharmaceutical formulation comprising a tetracyclic compound as claimed in claim 1 together with a pharmaceutically acceptable carrier or diluent therefor.

17. A method of treating sepsis or rheumatoid arthritis in a a mammal wherein the method comprises administering to said mammal a therapeutically effective amount of a tetracyclic compound as claimed in claim 1.

18. A pharmaceutical formulation containing a therapeutically effective amount of a compound of claim 1 for the treatment of sepsis or rheumatoid arthritis.

* * * * *